(12) United States Patent
Fidler et al.

(10) Patent No.: US 8,999,934 B2
(45) Date of Patent: Apr. 7, 2015

(54) TREATMENT OF ASTROCYTES-TUMOR CELLS INHIBITORS OF ENDOTHELIN RECEPTORS

(75) Inventors: Isaiah Fidler, Houston, TX (US); Sun-jin Kim, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/390,072

(22) PCT Filed: Aug. 9, 2010

(86) PCT No.: PCT/US2010/044832
§ 371 (c)(1),
(2), (4) Date: Feb. 10, 2012

(87) PCT Pub. No.: WO2011/019630
PCT Pub. Date: Feb. 17, 2011

(65) Prior Publication Data
US 2012/0144510 A1 Jun. 7, 2012

Related U.S. Application Data

(60) Provisional application No. 61/232,687, filed on Aug. 10, 2009.

(51) Int. Cl.
| | |
|---|---|
| *A61K 31/506* | (2006.01) |
| *A61K 31/337* | (2006.01) |
| *A01K 67/027* | (2006.01) |
| *A61K 31/4188* | (2006.01) |
| *C12N 5/079* | (2010.01) |
| *C12N 5/09* | (2010.01) |
| *G01N 33/50* | (2006.01) |

(52) U.S. Cl.
CPC ............ *A61K 31/337* (2013.01); *A01K 67/027* (2013.01); *A01K 2227/105* (2013.01); *A01K 2267/0331* (2013.01); *A61K 31/4188* (2013.01); *A61K 31/506* (2013.01); *C12N 5/0622* (2013.01); *C12N 5/0693* (2013.01); *C12N 2502/08* (2013.01); *C12N 2502/30* (2013.01); *G01N 33/5008* (2013.01)

(58) Field of Classification Search
None
See application file for complete search history.

(56) References Cited

U.S. PATENT DOCUMENTS

2013/0310407 A1 11/2013 Regenass

FOREIGN PATENT DOCUMENTS

| CN | 1780627 | 5/2006 |
|---|---|---|
| CN | 101039673 | 9/2007 |
| WO | 02/053557 | 7/2002 |
| WO | 2004/035057 | 4/2004 |
| WO | 2004/096224 | 11/2004 |
| WO | 2007/031933 A2 | 3/2007 |
| WO | 2009/104149 | 8/2009 |
| WO | 2012/104822 | 8/2012 |
| WO | WO 2012/104822 | 8/2012 |

OTHER PUBLICATIONS

Kefford et al., Invest New Drugs, 25:247-252, published online Oct. 5, 2006.*
Addeo, Raffaele et al., "Phase 2 Trial of Temozolomide Using Protracted Low-dose and Whole-brain Radiotherapy for Nonsmall Cell Lung Cancer and Breast Cancer Patients with Brain Metastases," Cancer (2008) vol. 113, No. 9, pp. 2524-2531.
Bagnato, Anna et al., "The endothelin axis in cancer: the promise and the challenges of molecularly targeted therapy," Canadian Journal of Physiology and Pharmacology (2008) vol. 86, No. 8, pp. 473-484.
Dreau, Didier et al., "Bosentan inhibits tumor vascularization and bone metastasis in an immunocompompetent skin-fold chamber model of breast carcinoma cell metastasis," Clinical and Experimental Metastasis (2006) vol. 23, pp. 41-53.
Jiao, Wen-Jie et al., "Effect of endothelin-1 in esophageal squamous cell carcinoma invasion and its correlation with cathepsin B," World Journal of Gastroenterology (2007) vol. 13, No. 29, pp. 4002-4005.
Rosano, Laura et al., "Endothelin-1 Induces Tumor Proteinase Activation and Invasiveness of Ovarian Carcinoma Cells," Cancer Research (2001) vol. 61, No. 22, pp. 8340-8346.
Rosano, Laura et al., "ZD4054, a specific antagonist of the endothelin A receptor, inhibits tumor growth and enhances paclitaxel activity in human ovarian carcinoma in vitro and in vivo," Molecular Cancer Therapeutics (2007) vol. 6, No. 7, pp. 2003-2011.
Rosano, Laura et al., "B-Arrestin links endothelin A receptor to B-catenin signaling to induce ovarian cancer cell invasion and metastasis," Proceedings of the National Academy of Sciences (2009) vol. 106, No. 8, pp. 2806-2811 and Supporting Information (pp. 1-9).
Smollich, M. et al., "Selective ETaR antagonist atrasentan inhibits hypoxia-induced breast cancer cell invasions," Breast Cancer Research and Treatment (2008) vol. 108, No. 2, pp. 175-182.
Uings, I.J. et al., "Cell receptors and cell signalling," Journal of Clinical Pathology/Molecular Pathology (2000) vol. 53, pp. 295-299.
Yakushiji, M. et al., "Recent Therapeutic Strategy for Advanced Ovarian Cancer," Japanese Journal of Clinical Oncology (1999) vol. 45, No. 8, pp. 949-951, English Abstract only.
Japanese Office Action/Rejection for JP 2012-524769 mailed Aug. 20, 2014.
Taiwanese Office Action for TW Patent Application 099126507 dated Aug. 20, 2014.
Wang, Duolao et al., "Clinical Trials: A Practical Guide to Design, Analysis and Reporting," 2005, Remedica Publishing, London, 498 pages.

(Continued)

*Primary Examiner* — Robert C Hayes
(74) *Attorney, Agent, or Firm* — Hunton & Williams LLP

(57) ABSTRACT

The disclosure relates to an endothelin receptor antagonist for use in the prevention or treatment of brain metastases in combination with a cytotoxic chemotherapy agent, radiotherapy or both. The endothelin receptor antagonist may for example be bosentan, macitentan or a mixture of bosentan and macitentan.

13 Claims, 22 Drawing Sheets

(56) References Cited

OTHER PUBLICATIONS

Edge, S. et al., "AJCC Cancer Staging Manual," 2010, Springer Publishing, 7th Edition (preface) 3 pages.

Kim, Sun-Jin et al., "Macitentan (ACT-064992), A Tissue-Targeting Endothelin Receptor Antagonist, Enhances Therapeutic Efficacy of Paclitaxel by Modulating Survival Pathways in Orthotopic Models of Metastatic Human Ovarian Cancer," Neoplasia. (2011), vol. 13, No. 2, pp. 167-179.

Aubert, John-David et al., "Expert Opinion: Therapeutic Potential of Endothelin Receptor Modulators: Lessons from Human Clinical Trials," (2009), vol. 13, No. 9, pp. 1069-1084.

Singapore Patent Application No. 2012009338 Office Action with Search Report and Written Opinion dated May 23, 2014, (21 pages).

Akhavan, Ardavan et al.; "Endothelin receptor a blockade enhances taxane effects in prostate cancer"; Neoplasia, vol. 8, No. 9, pp. 725-732, Sep. 2006.

Bagnato, A. et al.; "The endothelin axis in cancer"; International Journal of Biochemistry and Cell Biology, vol. 40, No. 8, pp. 1443-1451, Jan. 1, 2008.

Bolstad, B.M. et al., "A Comparison of Normalization Methods for High Density Oligonucleotide array data based on Variance and Bias," Bioinformatics, vol. 19, No. 2 pp. 185-193, 2003.

Breu, V. et al., "In vitro characterization of Ro 46-2005, a novel synthetic non-peptide endothelin antagonist of ETA and ETB receptors," FEBS Letters, vol. 334, No. 2, pp. 210-214, Nov. 15, 1993.

Carden, C.P. et al., "Eligibility of Patients with Brain Metastases for Phase I Trials; Time for a Rethink?" The Lancet Oncology, vol. 9, Issue 10, pp. 1012-1017, Oct. 2008.

Cavaliere, R. et al., "Chemotherapy and Cerebral Metastases: Misperception or Reality?" Neurosurg Focus from the American Association of Neurological Surgeons, vol. 22, No. 3:E6, 2007.

Chelouche Lev, Dina et al., "Inhibition of Platelet-Derived Growth Factor Receptor Signaling Restricts the Growth of Human Breast Cancer in the Bone of Nude Mice," Clinical Cancer Research, vol. 11, pp. 306-314, Jan. 1, 2005.

Chen Yiqi et al. "A Novel Target in Tumor Therapy: Endothelin Axis." Progress in Pharmaceutical Sciences, vol. 29, No. 2, pp. 62-68, 2005. (English Abstract).

Chiappori, Alberto A. et al; "Phase I/II study of atrasentan, an endothelin A receptor antagonist, in combination with paclitaxel and carboplatin as first-line therapy in advanced non-small cell lung cancer;" Clinical Cancer Research: An Official Journal of the American Association for Cancer Research; vol. 14, No. 5, pp. 1464-1469, Mar. 1, 2008.

Cory, A.H. et al., "Use of an Aqueous Soluble Tetrazolium/Formazan Assay for Cell Growth Assays in Culture," Cancer Communication, vol. 3, No. 7, pp. 207-212, Jul. 1991.

Dull, Tom et al., "A Third-Generation Lentivirus Vector with a Conditional Packaging System," Journal of Virology, vol. 72, No. 11, pp. 8463-8471, 1998.

Egidy, G. et al., "The Endothelin System in Human Glioblastoma," Laboratory Investment, vol. 80, pp. 1681-1689, 2000.

Fan, Dominic et al., "Enhancement of Murine Tumor Cell Sensitivity to Adriamycin by Presentation of the Drug in Phosphatidylcholine-Phosphatidylserine Liposomes," Cancer Research, vol. 50, pp. 3619-3626, 1990.

Fitzgerald, D.P. et al., "Reactive glia are Recruited by Highly Proliferative Brain Metastases of Breast Cancer and Promote Tumor Cell Colonization," Clinical and Experimental Metastasis, vol. 25, pp. 799-810, 2008.

Fonseca, Paula Candida et al., "Flow Cytometry Analysis of Gap Junction-Mediated Cell-Cell Communication: Advantages and Pitfalls" Cytometry, vol. 69A, pp. 487-493, 2006.

Galipeau, Jacques et al., "Vesicular Stomatitis Virus G Pseudotyped Retrovector Mediates Effective in Vivo Suicide Gene Delivery in Experimental Brain Cancer," Cancer Research, vol. 59, pp. 2384-2394, 1999.

Iglarz, M. et al., "Pharmacology of Macitentan, An Orally Active Tissue-Targeting Dual Endothelin Receptor Antagonist," Journal of Pharmacology and Experimental Therapeutics, vol. 327, No. 3, pp. 736-745, 2008.

Joyce, Johanna and Pollard, Jeffrey W., "Microenvironmental Regulation of Metastasis," Nature Reviews Cancer, vol. 9, No. 4, pp. 239-252, Apr. 2009.

Juanyin, J. et al., "Noninvasive imaging of the functional effects of anti-VEGF therapy on tumor cell extravasation and regional blood vol. in an experimental brain metastasis model," Clinical and Experimental Metastasis, vol. 26, No. 5, pp. 403-414, EPub, Mar. 11, 2009.

Kefford, Richard et al.; "A Phase II study of bosentan, a dual endothelin receptor antagonist, as monotherapy in patients with stage IV metastatic melanoma;" Investigational New Drugs; The Journal of New Anticancer Agents, vol. 25, No. 3, pp. 247-252, Oct. 5, 2006.

Kim, Sun-Jin et al., "Targeting Platelet-Derived Growth Factor Receptor on Endothelial Cells of Multidrug-Resistant Prostate Cancer," Journal of National Cancer Institute, vol. 98, No. 11, pp. 783-793, 2006.

Langley, Robert et al., "Activation of the Platelet-Derived Growth Factor-Receptor Enhances Survival of Murine Bone Endothelial Cells," Cancer Research, vol. 64, pp. 3727-3730, 2004.

Langley, Robert et al., "Generation of an Immortalized Astrocyte Cell Line from $H-2K^b$-tsA58 Mice to Study the Role of Astrocytes in Brain Metastasis," International Journal of Oncology, vol. 35, pp. 665-672, 2009.

Lin, J.H. et al., "Gap-Junction-mediated propagation and amplification of cell injury," Nature Neuroscience, vol. 1, No. 6, pp. 494-500, 1998.

Lin, J.H. et al., "Reactive Astrocytes Protect Melanoma Cells from Chemotherapy by Sequestering Intracellular Calcium through Gap Junction Communication Channels," Neoplasia, vol. 12, pp. 748-754, 2010.

Löscher, W. et al., "Drug Resistance in Brain Diseases and the Role of Drug Efflux Transporters," Nature Reviews Neuroscience, vol. 6, pp. 591-602, 2005.

Maher, E.A. et al., "Brain Metastasis: Opportunities in Basic and Translational Research," Cancer Research, vol. 69, pp. 6015-6020, 2009.

Mucke, H.A., "Small-Molecule Endothelin Receptor Antagonists: A Review of Patenting Activity Across Therapeutic Areas," IDrugs, vol. 12, No. 6, pp. 366-375, 2009.

Negoescu, Adrien, "In Situ Apoptotic Cell Labeling by the TUNEL Method: Improvement and Evaluation on Cell Preparations," The Journal of Histochemistry and Cytochemistry, vol. 44, No. 9, pp. 959-968, 1996.

Nelson, J.B. et al., "Phase 3: Randomized, Controlled Trial of Atrasentan in Patients with Nonmetastatic, Hormon-Refractory Prostate Cancer," Cancer, vol. 113, No. 9, pp. 2376-2378, Nov. 1, 2008.

Nelson, J.B. et al., "Phase 3: Randomized, Controlled Trial of Atrasentan in Patients with Nonmetastatic, Hormon-Refractory Prostate Cancer," Cancer, vol. 113, No. 9, pp. 2478-2487, Sep. 10, 2008.

Phuphanich, Surasak et al., "Phase I safety study of escalating doses of atrasentan in adults with recurrent malignant glioma;" Neuro-Oncology, vol. 10, No. 4, pp. 617-623, Aug. 4, 2008.

Platta, C.S. et al., "Current Treatment Strategies for Brain Metastasis and Complications From Therapeutic Techniques," American Journal of Clinical Oncology, vol. 33, pp. 398-407, 2010.

Seute, T. et al.; "Response of Asymptomatic Brain Metastases From Small-Cell Lung Cancer to Systemic First-Line Chemotherapy," Journal of Clinical Oncology, vol. 24, pp. 2079-2083, 2006.

Van Den Bent, M.J., "The Role of Chemotherapy in Brain Metastases." European Journal of Cancer, vol. 39, pp. 2114-2120, 2003.

Vatter, H. et al., "Cerebrovascular characterization of clazosentan, the first nonpeptide endothelin receptor antagonist shown to be clinically effective for the treatment of cerebral vasospasm. Part II: effect on endothelin(B) receptor-mediated relaxation," J. Neurosurg., vol. 102, No. 6, pp. 1108-1114, Jun. 2005.

Wade, M.H. et al., "A fluorescence photobleaching assay of gap junction-mediated communication between human cells," Science, vol. 232, No. 4749, pp. 525-528, Apr. 25, 1986.

(56) References Cited

OTHER PUBLICATIONS

Yano, Seiji et al., "Expression of vascular endothelial growth factor is necessary but not sufficient for production and growth of brain metastasis," Cancer Research, vol. 60, No. 17, pp. 4959-4967, 2000.

Yano, Seiji et al., "Treatment for malignant pleural effusion of human lung adenocarcinoma by inhibition of vascular endothelial growth factor receptor tyrosine kinase phosphorylation," Clinical Cancer Research, vol. 6, pp. 957-965, 2000.

Yoshimine, Toshiki et al., "Immunohistochemical study of metastatic brain tumors with astroprotein (GFAP), a glia-specific protein. Tissue architecture and the origin of blood vessels," Journal of Neurosurgery, vol. 62, No. 3, pp. 414-418, Mar. 1985.

Zamal Loris et al., "Supravital Exposure to Propidium Iodide Identifies Apoptosis on Adherent Cells," Cytometry, vol. 44, pp. 57-64, 2001.

Zhang, M., et al., "Reactions of Astrocytes and Microglial Cells Around Hematogenous Metastases of the Human Brain - Expression of Endothelin-Like Immunoreactivity in Reactive Astrocytes and Activation of Microglial Cells," Journal of Neurological Science, vol. 134, pp. 26-32, 1995.

Zhang, R.D., et al., "Differential Permeability of the Blood-Brain Barrier in Experimental Brain Metastases Produced by Human Neoplasms Implanted in Nude Mice," American Journal of Pathology, vol. 141, pp. 1115-1124, 1992.

* cited by examiner

Increased expression of ET$_A$-R in MDA231 human breast cancer cells co-cultured with astrocytes but not with fibroblasts (3T3)

1. MDA231 alone
2. MDA231 + Astrocyte-GFP
3. MDA231 + 3T3-GFP

Expression of pAKT by MDA231 human breast cancer cells co-cultured with astrocytes/Taxol

Green = MDA231
Red = pAkt
Blue = nucleus

Mouse model
CD31/ET$_B$R/DAPI

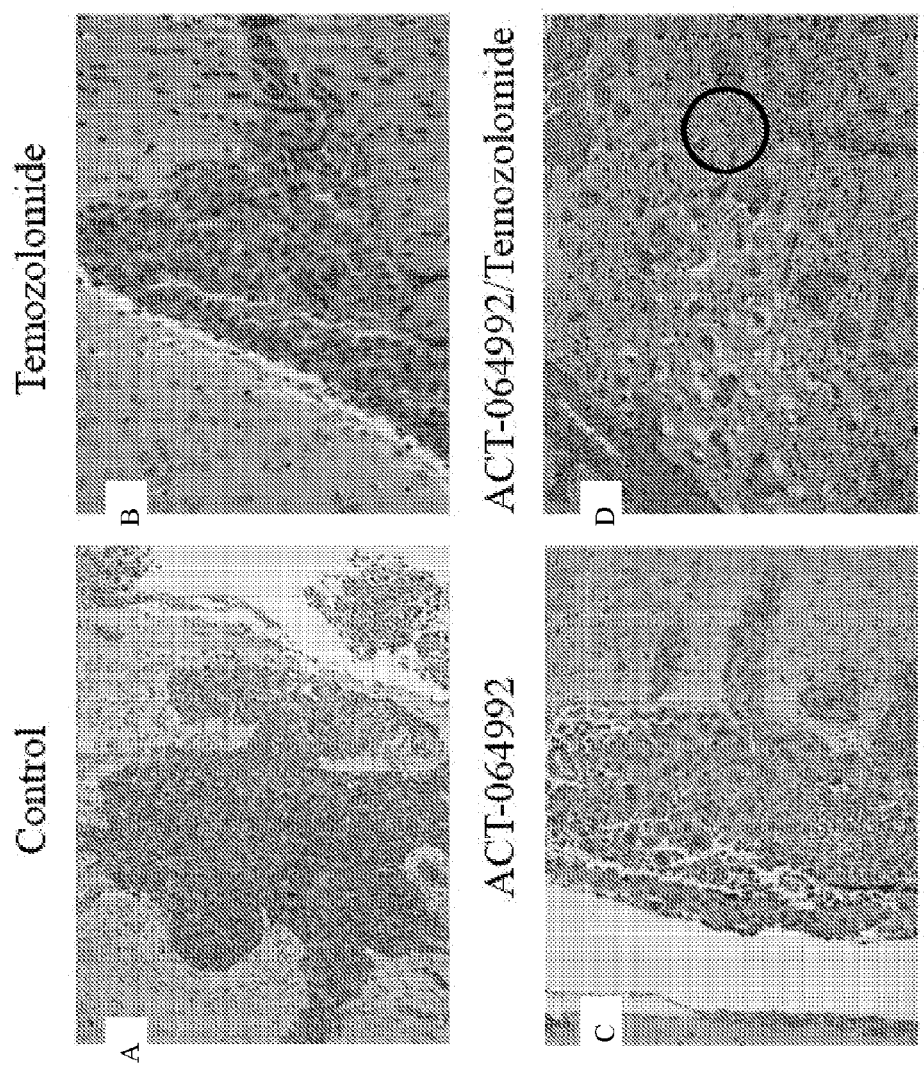
FIGURE 18 A-D

TREATMENT OF ASTROCYTES-TUMOR CELLS INHIBITORS OF ENDOTHELIN RECEPTORS

CROSS-REFERENCE TO RELATED APPLICATIONS

This application is the national phase application of PCT/US2010/044832, filed Aug. 9, 2010, which claims the benefit of U.S. Provisional Patent Application 61/232,687, filed Aug. 10, 2009, the contents of each are hereby incorporated by reference in their entirety.

BACKGROUND

Brain metastasis is one of the most difficult challenges facing oncology. Metastatic tumors are resistant to most chemotherapy agents. The treatments for brain metastasis are primarily whole brain and focused radiotherapy, with surgical resection of tumors in a minority of cases. Most chemotherapy regimens involve 2-3 agents such as cisplatin, cyclophosphamide, etoposide, teniposide, mitomycin, irinotecan, vinorelbine, etoposide, ifosfamide, temozolomide and fluorouracil (5-FU). These are administered in combination with radiotherapy. The effect of these chemotherapies on prolonging survival is generally less than a year. A fairly new chemotherapy for brain tumors is temozolomide used with whole-brain irradiation. Results are preliminary but temozolomide appears to have some limited effect on the response rate compared to radiation alone and appears to have some clinical activity in combination with radiation in phase II trials.

Despite intense efforts, the limited medical options available for brain metastasis have remained poor and too often more palliative than therapeutically effective. This state of affairs has been long recognized but, to date, significant advances have not materialized. Consequently, there is a great and present medical need for new therapeutic approaches and pharmaceuticals effective at treating brain metastasis.

The disclosure below discusses endothelin receptor antagonists in relation to brain metastasis. Endothelin-1 (hereafter "ET-1"), a vasoactive peptide, is produced primarily in endothelial, vascular smooth muscle, and epithelial cells. ET-1 exerts its physiological effect via two high-affinity G-protein-coupled receptors, the endothelin-A (hereafter "$ET_A$") and the endothelin-B (hereafter "$ET_B$") receptors. Endothelin receptor antagonists (ERAs) are a well established class of compounds capable of inhibiting these endothelin receptors (hereafter "ETRs"). Within this class are subclasses of antagonists specific to $ET_A$ or $ET_B$ and a subclass effective against both (dual specificity). One member of the dual specificity subclass, bosentan, is currently approved for use in treating pulmonary arterial hypertension.

Certain ERAs have been investigated for use in cancer therapy. [Nelson J B, et al., Phase 3, randomized, controlled trial of atrasentan in patients with nonmetastatic, hormone-refractory prostate cancer. Cancer, 2008 Nov. 1; 113(9):2376-8.; Chiappori A A, et al. Phase I/II study of atrasentan, an $ET_A$ receptor antagonist, in combination with paclitaxel and carboplatin as first-line therapy in advanced non-small cell lung cancer. Clin Cancer Res, 2008 Mar. 1; 14(5):1464-91 These studies have largely excluded patients with active brain metastasis. Ibid. This exclusion is done on the general view that existing brain metastases will not respond to treatment and, thus, morbidity and symptoms due to these metastases would mask the effects of the test treatment on the primary tumor, [Carden C P, et al., Eligibility of patients with brain metastases for phase I trials: time for a rethink? *The Lancet Oncology*, Vol 9, Issue 10, Pages 1012-1017, October 2008 doi:10.1016/S1470-2045(08)70257-2.] This standard clinical trial design strategy serves to emphasize the general expectation that therapies effective against primary tumors and even non-brain metastasis tumors will fail to effect brain metastasis tumors.

DETAILED DESCRIPTION

Definitions

Figure 1:
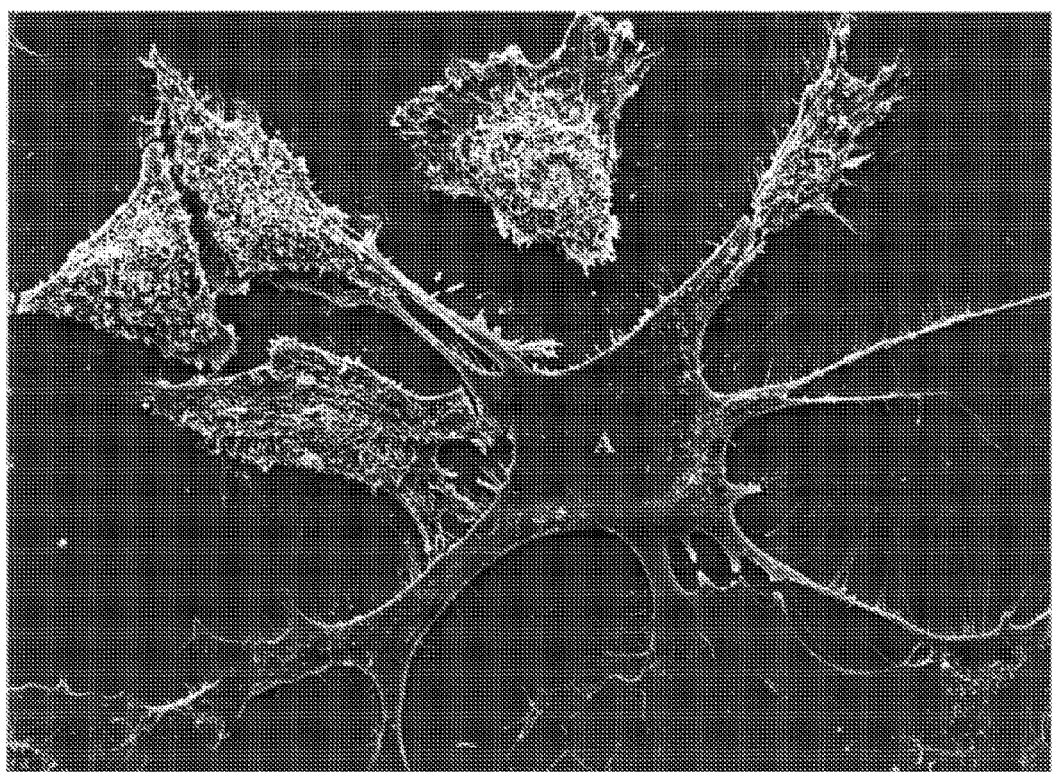
FIG. 1: In vitro culture of MDA-MB-231 breast cancer cells (T) and murine astrocytes (A) were evaluated by scanning electron microscopy. Direct contact between the astrocytes (extending pods-feet) and tumor cells is evident.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "containing", "including" and "comprising" are interchangeable and one of skill in the art is cognizant that these terms are open ended terms.

The term "treating" and "treatment" as used herein refers to administering to a subject a therapeutically effective medical intervention, such as chemotherapy, so that the subject has an improvement in the parameters relating to a cancer. The improvement is any observable or measurable improvement including changes in the size of a cancer tumor, reduction in the rate of growth of a cancer tumor, or subjective or objective measures of pain associated with a cancer tumor. Thus, one of skill in the art realizes that a treatment may improve the patient's condition but may not be a complete cure of the disease.

The term "effective amount" or "therapeutically effective amount" as used herein refers to an amount that results in an improvement or remediation of the symptoms of the disease or condition.

The term "existing brain metastasis tumor" as used herein refers to a multi-celled brain tumor and brain metastasis surrounded by and infiltrated with GFAP-positive astrocytes. Existing brain metastatic tumors are of two clinically distinct types, micrometastases, which are too small to be visualized by radiological means, and visible metastases, which are those tumors large enough to be discernable by clinical radiological means, such as magnetic resonance imaging, computerized tomography, or positron emission tomography. These metastatic lesions are distinct from metastatic cancer cells in the systemic circulation and single cancer cells extravasating into brain tissue or quiescently residing therein. [See generally Johanna A. Joyce & Jeffrey W. Pollard, Microenvironmental regulation of metastasis, Nat Rev Cancer 9, 239-252 (April 2009)|doi:10.1038/nrc2618.]

"Micrometastasis" as used herein is preferably defined as a group of confluent cancer cells measuring from greater than 0.2 mm and/or having greater than 200 cells to 2 mm in maximum width. More preferably "micrometastasis" is defined as a group of confluent cancer cells from 0.2 mm to 2 mm in maximum width. See The AJCC Cancer Staging Manual and Handbook, $7^{th}$ ed. (2010), Edge, S. B.; Byrd, D. R.; Compton, C. C.; Fritz, A. G.; Greene, F. L.; Trotti, A. (Eds.), ISBN: 978-0-387-88440-0. An alternative preferred definition of "micrometastasis" is a confluent group of at least 1000 cancer cells and at least 0.1 mm in widest dimension up to 1 mm in widest dimension. Micrometastasis are generally not visible in standard contrast MRI imaging or other clinical imaging techniques. However, in certain cancers, radioactive antibodies directed to tumor selective antigens (e.g. Her2 for breast cancer metastasis) will allow visualization of micrometastasis. Other indirect detection methods include contrast media leakage at brain micrometastasis sites due to VEGF induced vascular leakage. Yano S; et al. (2000), Expression of vascular endothelial growth factor is necessary but not sufficient for production and growth of brain metastasis. Cancer research 2000; 60(17):4959-67. More sensitive imaging techniques may also be applied to detect micrometastases. For example, blood volume may be imaged by MRI using the alternative contrast agent USPIO (Molday Iron, Biopal, Worcester, Mass., sold as Molday ION™) to detect micrometastasis. JuanYin J, et al. Noninvasive imaging of the functional effects of anti-VEGF therapy on tumor cell extravasation and regional blood volume in an experimental brain metastasis model. Clin Exp Metastasis. 2009; 26(5): 403-14. Epub 2009 Mar. 11.

The term "astrocyte mediated protection" as used herein refers to the ability of an astrocyte to reduce the cytotoxicity of a chemical for another cell type in direct physical contact with the astrocyte. This physical contact includes astrocytes connected to cancer cells, in particular via gap junction communication (GJC).

The term "cytotoxic chemotherapy induced cell death" as used herein refers to the induction of apoptosis or necrotic cell death by a cytotoxic chemical. Most medically used chemotherapy agents function to kill rapidly dividing tumor cells this way.

The term "endothelin receptor antagonist" as used herein refers to the class of compounds recognized in the art as such, and in particular to a compound that, when submitted to the "Test for the determination of $ET_A$ or $ET_B$ $IC_{50}$" described in the present patent application, has an $IC_{50}$ equal or lower than 1 μM against $ET_A$, against $ET_B$ or against both $ET_A$ and $ET_B$. An ERA is a drug that blocks endothelin receptors from interaction with ET-1 or prevents an ETR from responding to bound ET-1. Two main kinds of ERAs exist: selective ERAs, such as sitaxentan, ambrisentan and atrasentan, which affect $ET_A$ receptors, and dual ERAs, such as bosentan, which affect both $ET_A$ and $ET_B$ receptors. Exemplary members of the ERA class of compounds may be found in the patent literature cited in [HAM Mucke "Small-molecule endothelin receptor antagonists: A review of patenting activity across therapeutic areas" IDrugs 2009 12:366-375.] Representative ERAs which have already been investigated in human clinical trials or approved for medical use include sitaxentan, tezosentan, clazosentan, abbrisentan, bosentan, macitentan (also known as ACT-064992) and/or atrasentan.

The term "$ET_A$ antagonist" as used herein refers a compound that, when submitted to the "Test for the determination of $ET_A$ or $ET_B$ $IC_{50}$" described in the present patent application, has an $IC_{50}$ equal or lower than 1 µM against $ET_A$.

The term "$ET_B$ antagonist" as used herein refers a compound that, when submitted to the "Test for the determination of $ET_A$ or $ET_B$ $IC_{50}$" described in the present patent application, has an $IC_{50}$ equal or lower than 1 µM against $ET_B$.

The term "dual endothelin receptor antagonist" or "dual ERAs" as used herein refers a compound that, when submitted to the "Test for the determination of $ET_A$ or $ET_B$ $IC_{50}$" described in the present patent application, has an $IC_{50}$ equal or lower than 1 µM against $ET_A$ and an $IC_{50}$ equal or lower than 1 µM against $ET_B$. Dual ERAs include bosentan and macitentan.

The term "cytotoxic chemotherapy agent" as used herein refers to a substance inducing apoptosis or necrotic cell death. Examples of cytotoxic chemotherapy agents which may be used in combination with ERAs in accordance to the present invention include:
  alkylating agents (for example mechlorethamine, chlorambucil, cyclophosphamide, ifosfamide, streptozocin, carmustine, lomustine, melphalan, busulfan, dacarbazine, temozolomide, thiotepa or altretamine);
  platinum drugs (for example cisplatin, carboplatin or oxaliplatin);
  antimetabolite drugs (for example 5-fluorouracil, capecitabine, 6-mercaptopurine, methotrexate, gemcitabine, cytarabine, fludarabine or pemetrexed);
  anti-tumor antibiotics (for example daunorubicin, doxorubicin, epirubicin, idarubicin, actinomycin-D, bleomycin, mitomycin-C or mitoxantrone); and
  mitotic inhibitors (for example paclitaxel, docetaxel, ixabepilone, vinblastine, vincristine, vinorelbine, vindesine or estramustine); and
  topoisomerase inhibitors (for example etoposide, teniposide, topotecan, irinotecan, diflomotecan or elomotecan).

"Super-sensitization" or "Super-sensitize" is defined as a relative increase in cell death caused by cytotoxic chemotherapy agent(s) in physical contact with astrocytes over that seen in cells either in the absence of astrocytes or with no direct physical contact with astrocytes.

"Simultaneously" or "simultaneous", when referring to a therapeutic use, means in the present application that the therapeutic use concerned consists in the administration of two or more active ingredients by the same route and at the same time.

"Separately" or "separate", when referring to a therapeutic use, means in the present application that the therapeutic use concerned consists in the administration of two or more active ingredients at approximately the same time by at least two different routes.

By therapeutic administration "over a period of time" is meant in the present application the administration of two or more ingredients at different times, and in particular an administration method according to which the entire administration of one of the active ingredients is completed before the administration of the other or others begins. In this way it is possible to administer one of the active ingredients for several days, weeks or months before administering the other active ingredient or ingredients. In this case, no simultaneous administration occurs.

Disclosure

In the brain parenchyma, the role of astrocytes in maintaining homeostasis is well recognized. Astrocytes enwrap every blood vessel with specialized end-feet and communicate with other brain cells, such as neurons. This unique structure allows astrocytes to transport essential nutrients, such as glucose and amino acids, from the circulation to dependent neurons, and glycolysis in astrocytes has been recently shown to regulate neuronal activity, the so called "neuron-astrocyte metabolic coupling." Under pathological conditions, such as hypoxia, ischemia, and degenerative conditions, astrocytes will become activated and express a protein designated GFAP. GFAP reactive astrocytes have been shown to protect neurons from various challenges and to rescue neurons from excitotoxicity produced by accumulation of glutamate. Activated astrocytes can also protect neurons from apoptosis produced by ethanol, hydrogen peroxide, and copper-catalyzed cysteine cytotoxicity.

Clinical brain metastases are commonly surrounded by and infiltrated by activated (GFAP-positive) astrocytes. [Yoshimine T, et al. (1985) Immunohistochemical study of metastatic brain tumors with astroprotein (GFAP), a glia-specific protein. Tissue architecture and the origin of blood vessels. J Neurosurg 62: 414-418.] The Inventors have confirmed this phenomenon is reproduced in a xenotransplantation model below.

Various embodiments of the present invention are presented thereafter:

1) The invention firstly relates to an endothelin receptor antagonist for use in the prevention or treatment of brain metastases in combination with a cytotoxic chemotherapy agent, radiotherapy or both.

2) According to one main variant of embodiment 1), the endothelin receptor antagonist will be for use in combination with a cytotoxic chemotherapy agent.

3) According to one sub-embodiment of embodiment 2), the cytotoxic chemotherapy agent will comprise (and in particular be) an alkylating agent.

4) In particular, the alkylating agent of embodiment 3) will be selected from the group consisting of mechlorethamine, chlorambucil, cyclophosphamide, iphosfamide, streptozocin, carmustine, lomustine, melphalan, busulfan, dacarbazine, temozolomide, thiotepa and altretamine.

5) According to another sub-embodiment of embodiment 2), the cytotoxic chemotherapy agent will comprise (and in particular be) a platinum drug.

6) In particular, the platinum drug of embodiment 5) will be selected from the group consisting of cisplatin, carboplatin and oxaliplatin.

7) According to yet another sub-embodiment of embodiment 2), the cytotoxic chemotherapy agent will comprise (and in particular be) an antimetabolite drug.

8) In particular, the antimetabolite drug of embodiment 7) will be selected from the group consisting of 5-fluorouracil, capecitabine, 6-mercaptopurine, methotrexate, gemcitabine, cytarabine, fludarabine and pemetrexed.

9) According to a further sub-embodiment of embodiment 2), the cytotoxic chemotherapy agent will comprise (and in particular be) an anti-tumor antibiotic.

10) In particular, the anti-tumor antibiotic of embodiment 9) will be selected from the group consisting of daunorubicin, doxorubicin, epirubicin, idarubicin, actinomycin-D, bleomycin, mitomycin-C and mitoxantrone.

11) According to another sub-embodiment of embodiment 2), the cytotoxic chemotherapy agent will comprise (and in particular be) a mitotic inhibitor.

12) In particular, the mitotic inhibitor of embodiment 11) will be selected from the group consisting of paclitaxel, docetaxel, ixabepilone, vinblastine, vincristine, vinorelbine, vindesine and estramustine.

13) According to yet another sub-embodiment of embodiment 2), the cytotoxic chemotherapy agent will comprise (and in particular be) a topoisomerase II inhibitor.

14) In particular, the topoisomerase II inhibitor of embodiment 13) will be selected from the group consisting of etoposide, teniposide, topotecan, irinotecan, diflomotecan and elomotecan.

15) In a preferred sub-embodiment of embodiment 2), the cytotoxic chemotherapy agent will be selected from the group consisting of paclitaxel, doxorubicin, vinblastine, vincristine, 5-fluorouracil, cisplatin, cyclophosphamide, etoposide, teniposide, mitomycin-C, irinotecan, vinorelbine, ifosfamide and temozolomide (and in particular from paclitaxel and temozolomide).

16) In particular, the cytotoxic chemotherapy agent of embodiment 15) will be selected from paclitaxel, temozolomide and a mixture of paclitaxel and temozolomide.

17) According to a preferred variant of embodiment 16), the endothelin receptor antagonist of embodiment 16) will be selected from the group consisting of bosentan, macitentan and a mixture of macitentan and bosentan (and will notably be macitentan).

18) The invention also relates to an endothelin receptor antagonist for use in combination with at least one of the cytotoxic chemotherapeutic agents mentioned in one of embodiments 2) to 17) and with radiotherapy.

19) According to a preferred embodiment of this invention, the endothelin receptor antagonist used in embodiments 1) to 18) will comprise (and in particular be) a dual endothelin receptor antagonist.

20) In particular, the dual endothelin receptor antagonist of embodiment 19) will be selected from the group consisting of bosentan, macitentan and a mixture of bosentan and macitentan.

21) In a particularly preferred embodiment, the dual endothelin receptor antagonist of embodiment 20) will be macitentan.

22) According to one variant of embodiments 1) to 21), the endothelin receptor antagonist and the cytotoxic chemotherapeutic agent will be administered separately.

23) According to another variant of embodiments 1) to 21), the endothelin receptor antagonist and the cytotoxic chemotherapeutic agent will be administered simultaneously.

24) According to yet another variant of embodiments 1) to 21), the endothelin receptor antagonist and the cytotoxic chemotherapeutic agent will be administered over a period of time.

25) According to yet another main variant of embodiment 1), the endothelin receptor antagonist will be for use in combination with radiotherapy (whereby this radiotherapy is preferably whole brain radiotherapy or stereotactic radiosurgery).

26) According to a preferred embodiment of this invention, the endothelin receptor antagonist used in embodiment 25) will comprise (and in particular be) a dual endothelin receptor antagonist.

27) In particular, the dual endothelin receptor antagonist of embodiment 26) will be selected from the group consisting of bosentan, macitentan and a mixture of bosentan and macitentan.

28) In a particularly preferred embodiment, the dual endothelin receptor antagonist of embodiment 27) will be macitentan.

29) In another main variant of this invention, the endothelin receptor antagonist for use with a cytotoxic chemotherapy agent according to one of embodiments 2) to 23) will be for use together with radiotherapy (whereby this radiotherapy is preferably whole brain radiotherapy or stereotactic radiosurgery).

30) Another main variant of this invention, combinable with any one or more of the foregoing embodiments 1) to 29), is an endothelin receptor antagonist for use in the treatment of an existing brain metastasis tumor in a subject wherein the existing brain metastasis tumor is a micrometastasis tumor such as micrometastasis tumor selected from the group consisting of a lung cancer, breast cancer, colon cancer, melanoma or renal carcinoma brain micrometastasis tumor.

31) The invention also relates to a method of inhibiting an astrocyte mediated protection of a brain metastasis cell, which method comprises administering an effective amount of an endothelin receptor antagonist to the brain metastasis cell and the astrocyte to inhibit the astrocyte mediated protection.

32) The invention further relates to the method of embodiment 31), which further comprises administering an effective amount of at least one cytotoxic chemotherapeutic agent to the brain metastasis cell.

33) The invention furthermore relates to the method of embodiment 31), which further comprises submitting the brain metastasis cell to radiotherapy (whereby this radiotherapy is preferably whole brain radiotherapy or stereotactic radiosurgery).

34) The invention moreover relates to the method of embodiment 31), which further comprises administering an effective amount of at least one cytotoxic chemotherapeutic agent to the brain metastasis cell and submitting the brain metastasis cell to radiotherapy (whereby this radiotherapy is preferably whole brain radiotherapy or stereotactic radiosurgery).

35) The invention furthermore relates to a method of manufacturing a medicament for use according to any of the foregoing 1) to 34) and any combinations thereof. Preferably, the medicament produced by the foregoing is further packaged in a commercial package with instruction for carrying out one or more of 1)-34), and any combinations thereof.

36) The invention further relates to an endothelin receptor antagonist for use in the reduction of the risk of and/or reducing the rate of expansion of brain metastases, including brain micrometastasis, in combination with a cytotoxic chemotherapy agent, radiotherapy or both, according to one or more of 1)-34), and any combinations thereof.

EXPERIMENTAL SECTION

Experiment 1

Immunofluorescent Analysis of Brain Metastasis

Materials and Methods

Experimental brain metastases were produced by the injection of human lung adenocarcinoma cells PC14Br4 into the internal carotid artery of nude mice (S1). Mice were killed 5 weeks later and tissue samples were processed in OCT compound for frozen section as previously described (S2). Tissues were sectioned (8-10 μm), mounted on positively charged slides, and air-dried for 30 minutes. Tissue fixation was performed using a protocol consisting of three sequential immersions in ice-cold solutions of acetone, 50:50 (v/v)

acetone:chloroform, and acetone (5 minutes each). Samples were then washed three times with PBS, incubated with protein blocking solution containing 5% normal horse serum and 1% normal goat serum in PBS for 20 minutes at room temperature, and then incubated with a 1:400 dilution of rabbit anti-GFAP polyclonal antibody (Biocare Medical, Concord, Calif.) for 18 hours at 4° C. The samples were rinsed four times with PBS for 3 minutes each and then incubated for 1 hour with a 1:1500 dilution of goat anti-rabbit Cy5 antibody (Jackson ImmunoResearch Laboratories, West Grove, Pa.). Control samples were labeled with an identical concentration of isotype control antibody and goat anti-rabbit Cy5 antibody. All samples were rinsed and then briefly incubated with sytox green nucleic acid stain (Eugene, Oreg.). The slides were mounted with a glycerol/PBS solution containing 0.1 mol/L propyl gallate (Sigma) to minimize fluorescent bleaching. Confocal images were collected on a Zeiss LSM 510 laser scanning microscope system (Carl Zeiss, Inc., Thornwood, N.Y.) equipped with a motorized Axioplan microscope, argon laser, HeNe laser, LSM 510 control and image acquisition software, and appropriate filters (Chroma Technology Corp., Brattleboro, Vt.).

18 Composite images were constructed with Photoshop software (Adobe Systems, Inc., Mountain View, Calif.).

Results

The results were determined from color images (not shown) of immunohistochemically reacted samples. Tumor cells were surrounded by and infiltrated with GFAP-positive (red) astrocytes. This experiment confirmed prior observations of astrocyte infiltration of clinical brain metastasis samples. The same infiltration by GFAP-positive astrocytes were seen with a syngenic murine mouse model. Immunohistochemical analysis of mouse Lewis lung carcinoma (3LL) in the brain of a C57 mouse. Dividing 3LL cells (PCNA-positive, blue) were infiltrated and surrounded by activated astrocytes (GFAP-positive, brown). Together, these experiments validated the murine-human xenograft model which reproduced the phenomenon seen in clinical human samples and in the syngenic mouse model. One aspect of the present invention is therefore an in vivo mouse-human brain metastasis cell model which is useful, for example, in studying the phenomenon of human metastatic brain cancer.

Experiment 2

Scanning Electron Microscopy Studies

Having established that murine astrocytes interact in vivo with human tumor cells in the formation of brain metastasis in the same way as is seen in primary human clinical specimens, the Inventors examined the interactions of these two cell types in vitro in a simplified co-culture system. It was uncertain whether such a system would result in any cell-to-cell interaction, much less having direct physiological relevance to the in vivo situation described above. It was therefore a surprising discovery that intercellular interactions between human metastatic cancer cell lines and murine astrocytes were achieved in vitro.

Materials and Methods

Cell Lines and Culture Conditions.

Human breast cancer cell line, MDA-231 (S3), a brain metastatic variant of human lung adenocarcinoma cell line PC14Br4 (Si) and murine NIH 3T3 fibroblasts were maintained as monolayer cultures in a complete Eagle's minimum essential medium (CMEM) supplemented with 10% fetal bovine serum (FBS; HyClone, Logan, Utah), L-glutamine pyruvate, nonessential amino acids, two-fold vitamin solution, and penicillin streptomycin (GIBCO/Invitrogen, Carlsbad, Calif.). All reagents used for tissue culture were free of endotoxin as determined by the limulus amebocyte lysate assay (Associate of Cape Cod, Woodshole, Mass.), and the cell lines were free of the following murine pathogens: *Mycoplasma* spp, Hantan virus, hepatitis virus, minute virus, adenovirus (MAD1, MAD2), cytomegalovirus, ectromelia virus, lactate dehydrogenase-elevating virus, polyma virus, and Sendai virus (assayed by the Research Animal Diagnostic Laboratory, University of Missouri, Columbia, Mo.). Cells used in this study were from frozen stock and all experiments were carried out within 10 in vitro passages after thawing.

Isolation and Maintenance of Murine Astrocytes.

Neonatal mice homozygous for a temperature-sensitive SV40 large T antigen (H-2 Kb-tsA58 mice; CBA/ca x C57BL/10 hybrid; Charles River Laboratories, Wilmington, Mass.) were euthanized in a carbon dioxide chamber, and the skin was prepared for surgery in standard fashion (S4). Sterile micro forceps (Roboz Surgical Instrument Co., Gaithersburg, Md.) were used to remove the skin from the skull, and microscissors were used to create a circular posterior incision from the opening of the left ear to the opening of the right ear. Another incision was made along the brain midline, and the skull was divided to allow access to the cranial cavity. The optic nerves were clipped and the brain removed with blunt forceps and placed into 100-mm ice-cold phosphate buffered saline (PBS). Whole neocortices were dissected, and the hippocampus and internal structures were removed to leave only the cortical sheets. The meninges were stripped away, and the cortical sheets were minced with a scalpel and digested for 30 minutes at 37° C. in Dulbecco's modified essential medium (DMEM) containing 0.1% collagenase (150 U/ml; Worthington Biochemical Corp., Lakewood, N.J.) and 40 pg/ml deoxyribonuclease (Sigma Chemical Co., St. Louis, Mo.). The cortical tissue was then triturated in DMEM containing 10% FBS and filtered through a 50-pm sterile mesh. The resulting single-cell suspension was plated onto 75-cm 2 tissue culture flasks that had been previously coated with 5 µg/ml mouse laminin (Sigma). The cells were allowed to grow for 7 days in DMEM containing 10% FBS and supplements (see above) in an atmosphere of 8% carbon dioxide (to achieve a proper buffering of pH at 33° C.). At this time, astroglial cells formed a confluent monolayer with neurons, oligodendrocytes, and fibroblasts growing on top. These contaminating cells were removed by rotary shaking the flasks overnight at 250 revolutions per minute in a warm room. The resulting cultures were composed of more than 95% astrocytes as determined by immunoreactivity with antibodies directed against GFAP. These cultures were expanded, the procedure was repeated, and the percentage of astrocytes in these cultures was determined to exceed 99%.

Scanning Electron Microscope Imaging of Cultured Tumor Cells and Astrocytes.

Human breast cancer MDA-MB-231 cells and murine astrocytes were plated in DMEM containing 5% FBS onto sterilized glass coverslips in 24 well plates at a density of $2.4 \times 10^4$ cells. After 48 hours, the coverslips were removed and fixed for 1 hour at room temperature in a solution containing 3% glutaraldehyde/2% parpformaldehyde/7.5% sucrose in 0.1 M cacodylate buffer (pH 7.3). The samples were then washed with 0.1 m cacodylate buffer and post-fixed for 1 hour with 1% cacodylate buffered osmium tetroxide containing 7.5% sucrose. The samples were washed with 0.1 M cacodylate buffer followed by distilled water and sequentially treated for 30 minutes in the dark with Millipore-filtered aqueous 1% tannic acid, washed in distilled water and Millipore-filtered 1% aqueous uranyl acetate for 1 hour in the dark.

The samples were rinsed thoroughly with distilled water, dehydrated through an ascending series of ethanols, and then transferred for 5 minutes each to a graded series of increasing concentrations of hexamethyldisilazane and allowed to air dry overnight. Samples were mounted onto double-thick carbon tabs (Ted Pella, Inc., Redding, Calif.) that had previously been mounted onto aluminum specimen mounts (Electron Microscopy Sciences, Ft. Washington, Pa.). The samples were then coated under vacuum using a Balzer MED 010 evaporator (Technotrade International, Manchester, N.H.) with platinum alloy for a thickness of 25 nm and then immediately flash carbon coated under vacuum. The samples were transferred to a desiccator for examination at a later date. Samples were examined using a JSM-5910 scanning electron microscope (JEOL, Inc., Peabody, Mass.) at an accelerating voltage of 5 kV.

Results

The results are shown in FIG. 1. In vitro culture of MDA-MB-231 breast cancer cells (T) and murine astrocytes (A) were evaluated by scanning electron microscopy. Direct contact between the astrocytes (extending pods-feet) and tumor cells is evident. A single astrocyte can contact multiple tumor cells. These appear to be fully formed gap junctions of the kind seen between astrocytes and neurons of the central nervous system. Similar results are seen with melanoma, breast cancer and lung cancer cell lines (not shown).

Experiment 3

Gap Junction Assays

To further validate the functional nature of the gap junctions shown in FIG. 1, The Inventors performed dye transfer experiments to ascertain whether the gap junction like structures seen in Experiment 2 were functional.

Materials and Methods

Gap Junction Communication.

Gap junction communication between recipient tumor cells (MDA-MB-231) and donor cells (astrocytes, 3T3 cells, MDA-MB-231) was analyzed by flow cytometry measuring the transfer of dye. Briefly, recipient cells (300,000 cells/well) were plated into a 6-well plate and cultured overnight. At that time, donor cells were labeled for 45 minutes with 1 green calcein-AM (Molecular Probes) followed by extensive washing. Donor cells (60,000 cells/well) were co-cultured for 5 hours with recipient cells either directly or in a transwell chamber (Transwell-Boyden Chamber, 0.4 p.m pore size; Costar, Corning, N.Y.). Cells were harvested, washed, fixed in ethanol, and analyzed by flow cytometry. Gap junction formation was calculated as the percent of shifted FITC peak (S9-S11).

Results

Figure 2:
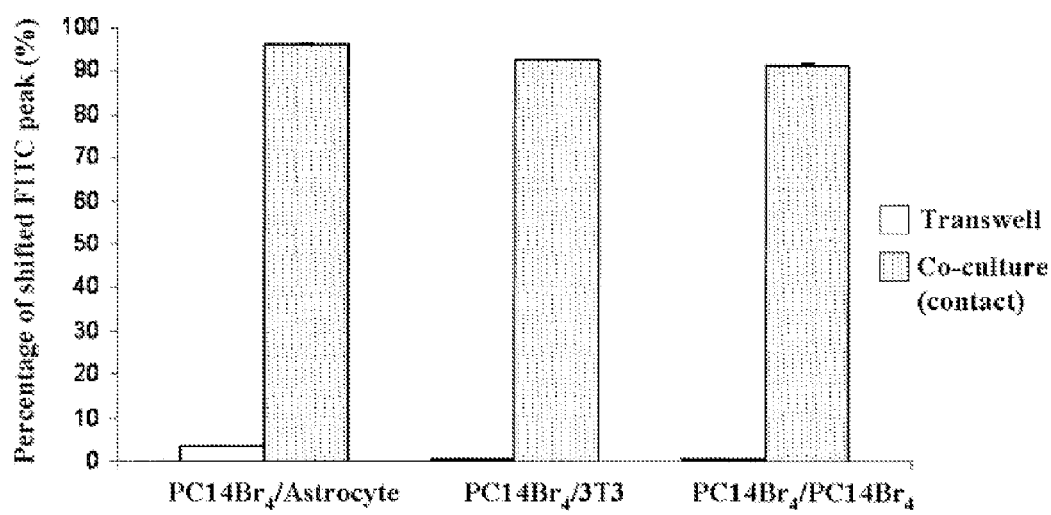
FIG. 2: The astrocyte-metastatic cancer cell co-cultures showed dye transfer between co-cultured cells.

As shown in FIG. 2, the astrocyte-metastatic cancer cell co-cultures showed dye transfer between co-cultured cells. The Inventors' co-culture system thus results in active gap junctions forming between murine astrocytes and human metastatic cancer cell lines. The control transwell experiments demonstrate this to be a genuine cell-cell interaction. A second aspect of the present invention is therefore an in vitro mouse astrocyte-human metastasis cell co-culture system which is useful, for example, in studying the phenomenon of human metastatic brain cancer interaction with astrocytes in a manipulable ex vivo setting.

Experiment 4

Chemoprotection Assays

Modeling of the chemoresistance of brain metastasis is and will be a major use for both the foregoing in vivo model system and the in vitro cell co-culture system. Because the cell based co-culture system is more amenable to experimental manipulation, it was further assessed to determine if the chemoresistance of brain metastases seen in vivo was replicated by the cell based culture system.

Material and Methods

In Vitro Co-Culture Chemoprotection Assay.

Astrocytes and NIH 3T3 fibroblasts were transfected with GFP genes as previously described (S5, S6). Target tumor cells, astrocytes, or 3T3 fibroblasts were harvested from a 60-70% confluent culture by a brief (2-minute) exposure to 0.25% trypsin in a 0.1% EDTA/PBS solution. The cells were dislodged by tapping the culture flasks briskly and resuspended in CMEM. The murine astrocytes, 3T3 fibroblasts, and tumor cells were plated alone or as co-culture at a tumor cell/astrocyte/3T3 cell ratio of 1:2 onto each of the 35-mm diameter well of the sterile 6-well tissue culture multi-well dish. The cells were allowed to adhere overnight in a humidified 37° C. incubator in an atmosphere of 6.4% carbon dioxide plus air. The cultures were then washed and incubated with fresh CMEM (negative control) or medium containing various concentrations of TAXOL® (Paclitaxel; NDC 0015-3476-30, Bristol-Myers Squibb, Princeton, N.J.) and other chemotherapeutic drugs (see below).

After 72 hours, the GFP labeled astrocytes or NIH 3T3 cells were sorted out and the apoptotic fraction of tumor cells was determined by propidium iodide staining and FACS analysis (see below). To determine whether direct contact between tumor cells and astrocytes (or fibroblasts serving as control) was a prerequisite to produce induction of resistance to chemotherapy, we performed the co-culture assay using a Transwell-Boyden chamber, i.e., plating the tumor cells in the chamber and the ImmortoAstrocytes (or fibroblasts) in the well. After 72 hours of incubation, the relative apoptotic index of the tumor cells was determined as described below.

In the second set of in vitro studies, we determined whether astrocyte-mediated induction of tumor cell resistance to chemotherapeutic drugs is transient or permanent. The human lung cancer PC14Br4 cells were co-cultured with either astrocytes or 3T3 fibroblasts in medium alone or medium containing 5 ng/ml paclitaxel. After 72 hours, the astrocytes or 3T3 cells were separated from tumor cells by FACS, and the relative apoptotic index of the tumor cells was determined in multiple wells by propidium iodide staining as described below. From parallel wells, we harvested surviving tumor cells and re-plated them on different monolayers of astrocytes or 3T3 cells. These co-cultures were of tumor cells first co-cultured with astrocytes and then with either astrocytes or 3T3 cells, or of tumor cells first cultured with 3T3 cells and then with either 3T3 cells or astrocytes. The second round of co-cultures then received media containing 5 ng/ml of paclitaxel. After 72 hours, the relative apoptotic index of tumor cells was determined by propidium iodide staining and FACS analysis.

Preparation for Propidium Iodide Staining and FACS Analysis.

The supernatant medium containing floating cells were collected from each dish into a 15-ml conical centrifuge tube. The attached cells were harvested by briefly exposing the cells to 0.25% trypsin in a solution containing 0.1% EDTA/PBS. Cells were combined with the corresponding supernatant medium. The samples were pelleted by centrifugation at 100 g for 5 minutes. The pellets were resuspended in 10 ml of HBSS and further pelleted at 100 g for 5 minutes. The samples were resuspended by vortex and the cells fixed in 1 ml of 1% paraformaldehyde for 10 minutes at room temperature. The samples were then transferred into polypropylene microcentrifuge tubes and the fixed cells were washed in 1 ml of PBS and then pelleted at 10,000 g for 1 minute. The pellets were resuspended by vortex and the cells fixed overnight in 1 ml of ethanol at −20° C. The cells were subsequently vortexed and pelleted by a microcentrifuge at 10,000 g for 1 minute. The samples were then vortexed and the pellets resuspended and stained in 300 of propidium iodide (50 µg/ml; Cat. P4864, Sigma) containing RNAse (15 µg/ml; Cat. A7973, Promega, Madison, Wis.) for 20-30 minutes at 37° C. The samples were finally transferred to 5-ml plastic culture tubes for FACS analysis using a Coulter EPICS Cytometer (Beckman Coulter, Inc., Fullerton, Calif.). Relative apoptotic index was determined by comparing the apoptotic index of tumor cells/ apoptotic index of tumor cells and ImmortoAstrocytes or tumor cells and NIH 3T3 fibroblasts×100(%) (S7).

Results

Figure 3:
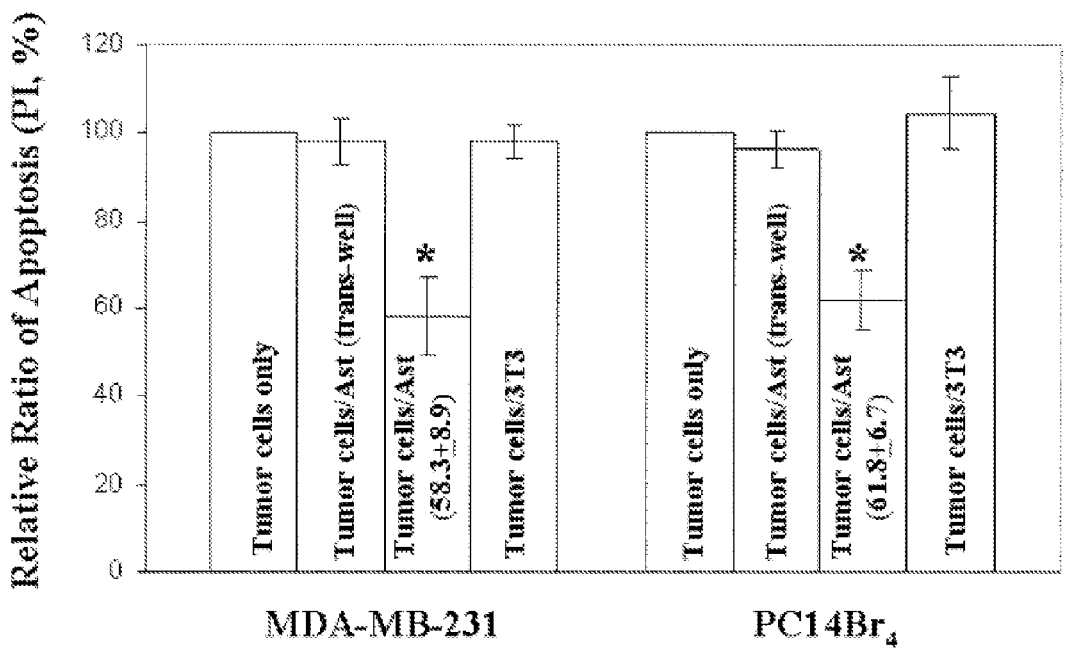
FIG. 3: Culturing of human MDA-MB-231 breast cancer cells or human PC14Br4 lung cancer cells with astrocytes (but not 3T3 fibroblasts) reduced the relative apoptotic index (increased resistance) of tumor cells incubated for 72 hours with paclitaxel (5 ng/ml) by 58.3+8.9% (mean±S.D., P<0.01) and 61.8±6.7% (mean±S.D., P<0.05), respectively (the apoptotic index was compared by the Student's t test)

Culturing of human MDA-MB-231 breast cancer cells or human PC14Br4 lung cancer cells with astrocytes (but not 3T3 fibroblasts) reduced the relative apoptotic index (i.e. increased chemoresistance) of tumor cells incubated for 72 hours with paclitaxel (5 ng/ml) by 58.3+8.9% (mean±S.D., P<0.01) and 61.8±6.7% (mean±S.D., P<0.05), respectively (the apoptotic index was compared by the Student's t test) (FIG. 3). This reduction was dependent on direct contact between tumor cells and astrocytes. The Inventors base this conclusion on the data showing that when tumor cells and astrocytes were separated by a semi-permeable membrane (Transwell-Boyden Chamber, 0.4 pm pore size membrane; Costar, Corning, N.Y.), the chemoprotective effect of astrocytes was not observed. Co-culture of tumor cells with 3T3 fibroblasts did not protect tumor cells from chemotherapy (FIG. 3). Co-culture of human tumor cells with an alternative control using fibroblasts isolated from the $H-2k^b$-tsA58 mouse also did not protect the tumor cells from chemotherapeutic agents (data not shown). Analogous results were seen using standard MTT assays to determine the degree of cytotoxicity (data not shown). [Cory A H, Owen T C, Barltrop J A, Cory J G (July, 1991) "Use of an aqueous soluble tetrazolium/ formazan assay for cell growth assays in culture." Cancer Communications 3 (7): 207-212.]

These data validate the cell based co-culture system disclosed herein as reproducing the phenomenon of brain metastasis chemoresistance. The unexpected ability of the co-culture system to replicate chemoresistance thus renders it well suited for use in studying the mechanism of chemoresistance and potential therapeutic interventions for abrogating chemoresistance in existing brain metastasis in vivo.

Figure 4:
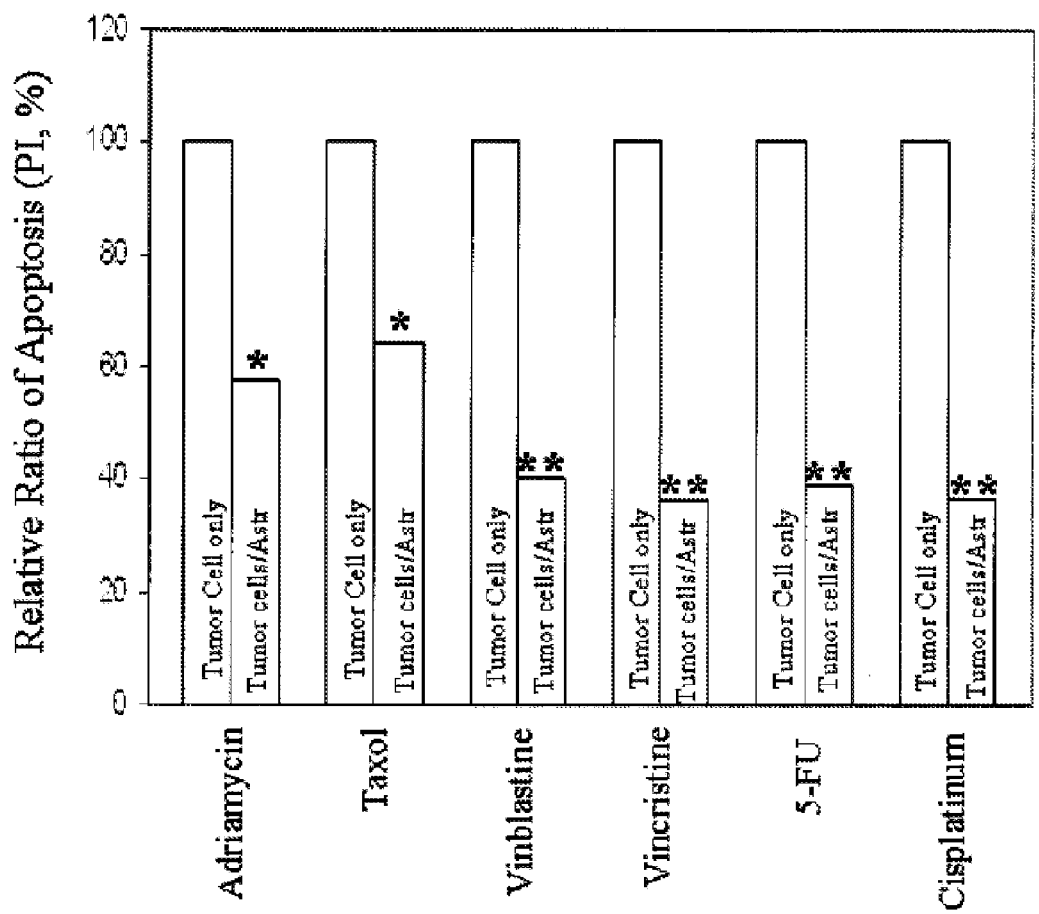
FIG. 4: Human lung cancer PC14Br4 cells were cultured alone or with astrocytes (direct cell to cell contact) in medium containing P-glycoprotein-associated Adriamycin (200 ng/ml), paclitaxel (5 ng/ml), vinblastine (3 ng/ml), vincristine (8 ng/ml), and P-glycoprotein-dissociated 5-FU (500 ng/ml) or cisplatinum (2.4 µg/ml)

To expand upon these initial experiments, the Inventors have tested several additional chemotherapy agents, representative of the major classes of drugs in use to day. Human lung cancer PC14Br4 cells were cultured alone or with astrocytes (direct cell to cell contact) in medium containing P-glycoprotein-associated Adriamycin (200 ng/ml), paclitaxel (5 ng/ml), vinblastine (3 ng/ml), vincristine (8 ng/ml), and P-glycoprotein-dissociated 5-FU (500 ng/ml) or cisplatinum (2.4 µg/ml). Co-culture with astrocytes induced significant (P<0.01) protection against all drugs (FIG. 4). This unexpected finding further validates the cell based co-culture system. The cell culture system demonstrates the robustness of the chemoresistance induced by astrocytes in a manner which is directly comparable to brain metastasis chemoresistance seen in vivo in the clinical setting. A third aspect of the present invention is therefore an in vitro cell based chemoresistance assay which is useful, for example, in studying the phenomenon of astrocyte mediated protection of brain metastasis cells from cytotoxic chemotherapy induced cell death. In particular embodiments the in vitro cell based chemoresistance assay may be used to screen one or more candidate chemotherapy agents to assess the degree of astrocyte mediated protection against the cytotoxic effects of the chemotherapy agents.

Figure 5:
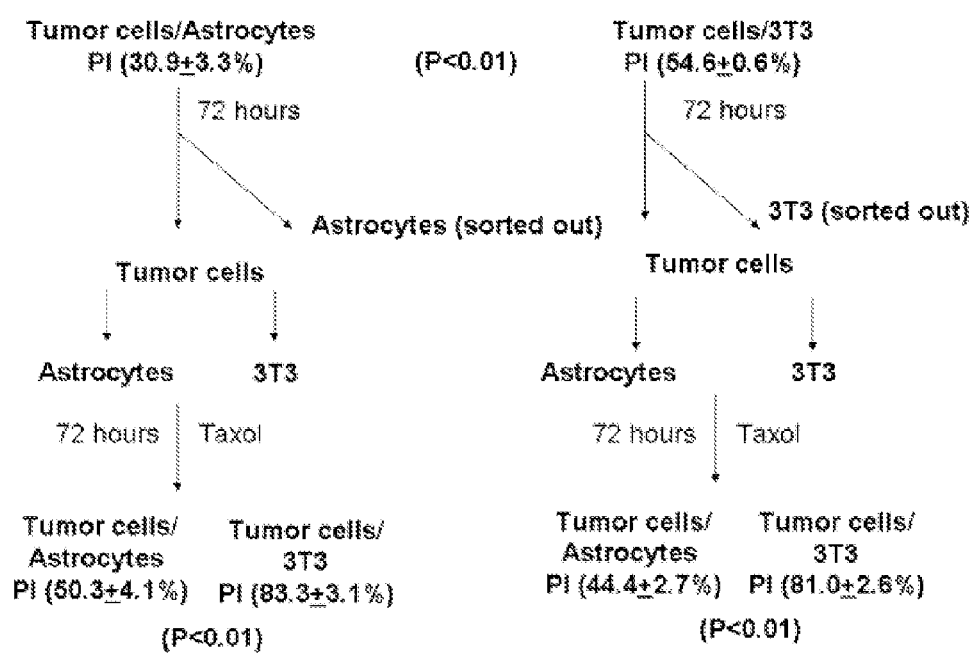
FIG. 5: Astrocyte-mediated protection of brain metastasis cells from cytotoxic chemotherapy-induced cell death does not last longer than 72 hours after direct astrocyte-brain metastasis cell contact is lost.
Figure 6:
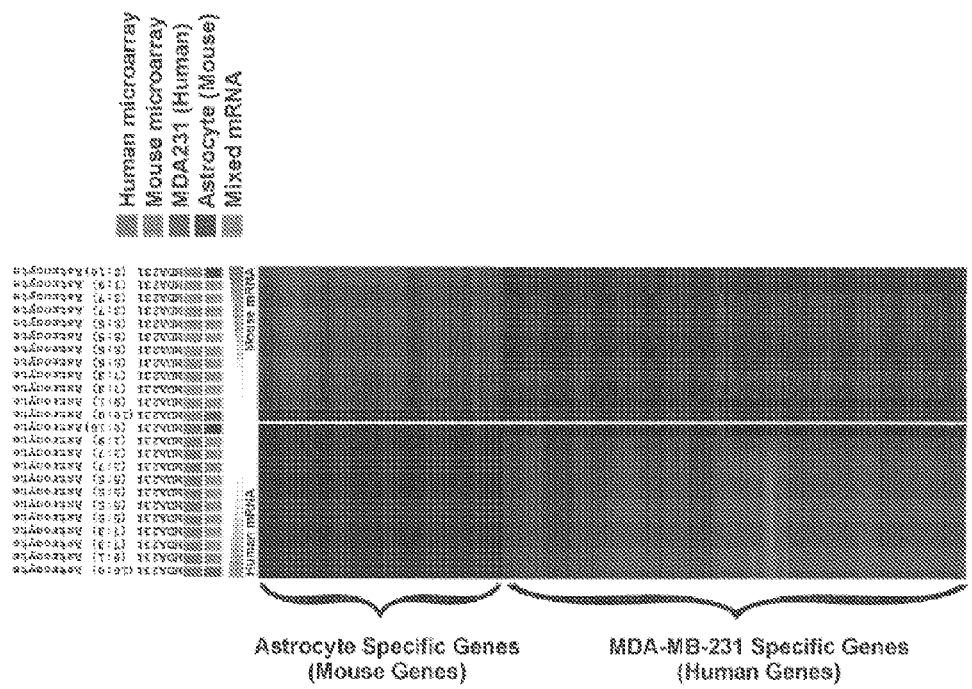
FIG. 6: Gene transcription profiling conditions distinguished between murine and human mRNA.

Additional experiments summarized in FIG. 5 demonstrate that astrocyte-mediated protection of brain metastasis cells from cytotoxic chemotherapy-induced cell death does not last longer than 72 hours after direct astrocyte-brain metastasis cell contact is lost. Further, cells having lost the protective effect afforded by prior astrocyte contact can be re-protected by a second co-culturing with astrocytes to reacquire astrocyte-mediated protection against the cytotoxic effects of the chemotherapy agents. This reflects the clinical observations of primary tumors and even other non-brain metastasis being chemoresponsive while their derived brain metastasis are chemoresistant.

Experiment 5

Mechanism of Astrocyte-Mediated Chemoresistance

The Inventors applied the above cell-based chemoresistance assay to investigate potential mechanisms underlying the phenomenon. Gene expression profiling plus Western blot confirmation of protein production were used to investigate astrocyte-mediated protection of brain metastasis cells from cytotoxic chemotherapy-induced cell death.

Materials and Methods

Gene expression profiles by RNA microarray analysis. In the first set of experiments, MDA-MB-231 or PC14Br4 cells were incubated alone, with murine astrocytes, or with NIH 3T3 fibroblasts in a 35-mm diameter 6-well plate (Cat. 353046, BD Falcon TM, San Jose, Calif.). To ascertain cell-to-cell contact, the ratio of tumor cells to murine astrocytes or NIH 3T3 cells was 1:2. After 72 hours, GFP-labeled murine astrocytes or fibroblasts were sorted out by FACS, and the tumor cells were processed for microarray analyses. In the second set of experiments, we determined whether the expression of genes associated with tumor cell resistance to chemotherapeutic drugs was dependent on a continuous contact with astrocytes. MDA-231 or PC14Br4 cells were co-cultured with either murine astrocytes or NIH 3T3 cells for 72 hours. The murine astrocytes or NIH 3T3 cells were sorted out, and tumor cells were either processed to determine gene expression profiles by microarray analyses or plated for a second round of co-culture with either murine astrocytes or fibroblasts. Thus, tumor cells first cultured with murine astrocytes were co-cultured again with murine astrocytes or with fibroblasts and, conversely, tumor cells initially cultured with fibroblasts were co-cultured again with fibroblasts or astrocytes. After a 72-hour incubation, murine astrocytes or fibroblasts were sorted out and the tumor cells were processed for microarray analyses.

Microarray Analyses.

Total RNAs (500 ng) were used for labeling and hybridization according to the manufacturer's protocols (Illumina, Inc., San Diego, Calif.). Briefly, cDNA was generated from total RNA using IlluminaR Total Prep RNA Amplification Kit (Applied Biosystem, Austin, Tex.). Next, in vitro transcription was carried out to incorporate biotin-labeled nucleotides into cRNA for 4 hours at 37° C. A total of 1500 ng of biotin-labeled cRNA was hybridized to Ilumina's SentrixR human 6-v2 Expression BeadChips at 58° C. overnight (16 hours) according to the manufacturer's instructions. The hybridized biotinylated cRNA was detected with 1 µg/ml cyanine 3-streptavidine (GE Healthcare, Piscataway, N.J.), and the BeadChips were scanned with Illumina BeadArray Reader (Illumina, Inc.). The results of microarray data were extracted with Bead Studio 3.7 (Illumina, Inc.) without any normalization or background subtraction. Gene expression data were normalized using quantile normalization method in LIMMA package in R (www.r-project.org) (S12). The expression level of each gene was transformed into a log 2 before further analysis. To select genes that are differentially expressed in two groups of tissues, we used a class comparison tool in BRB Array Tools (v 3.6; Biometrics Research Branch, National Cancer Institute, Bethesda, Md.) as a method for two sample 1-tests with the estimation of FDR.

Western Blot Analysis.

The Western blot was used to confirm the results of the microarray. Briefly, whole-cell lysates of FACS-sorted tumor cells were prepared using 1 ml of lysis buffer (10 mM Tris [pH 8.0], 1 mM EDTA, 0.1% SDS, 1% deoxycholate, 1% NP40, 0.14 M NaCl, 1 µg/ml leupeptin, 1 µg/ml aprotinin, and 1 µg/ml pepstatin) containing a protease inhibitor mixture (Roche, Indianapolis, Ind.). Samples containing equal amounts of protein (30 fag) were separated by electrophoresis on 4-12% Nu-PAGE gels (Invitrogen) and transferred to nitrocellulose membranes. After blocking with TTBS (TBS+0.1% Tween 20) containing 5% non-fat milk, the membranes were incubated at 4° C. overnight with mouse monoclonal antibody against BCL2 (1:1,000, BD PharMingen, San Diego, Calif.), rabbit polyclonal antibody against BCL2L1 (1:1,000, Cell Signaling, Beverly, Mass.), rabbit polyclonal antibody against TWIST (1:1000, Cell Signaling), mouse monoclonal antibody against glutathione S-transferase (1:1,000, BD PharMingen), and mouse monoclonal antibody against β-actin (Sigma). Blots were then exposed to horseradish peroxidase-conjugated secondary antibodies (1:3000) and visualized by the enhanced chemiluminescence system from Amersham (Piscataway, N.J.). Equal protein loading was confirmed by stripping the blots and re-probing them with an anti-13-actin antibody.

Statistical Analysis.

For statistical analysis of gene expression profiles, the expression level of each gene was transformed into a log 2 before further analysis. Class comparison tool in BRB Array Tools (v3.6; Biometrics Research Branch, National Cancer Institute, Baltimore, Md.) for a two-sample t test with the estimation of FDR was the method used to determine the statistical significance of differentially expressed genes between tumor cells co-cultured with different host cells. Genes for Venn diagram were selected by univariate test (two-sample t test) with multivariate permutation test (10,000 random permutations). We applied a cut-off P-value of less than 0.001 to retain genes whose expression is significantly different between two groups of tissues examined.

Results

Figure 7:
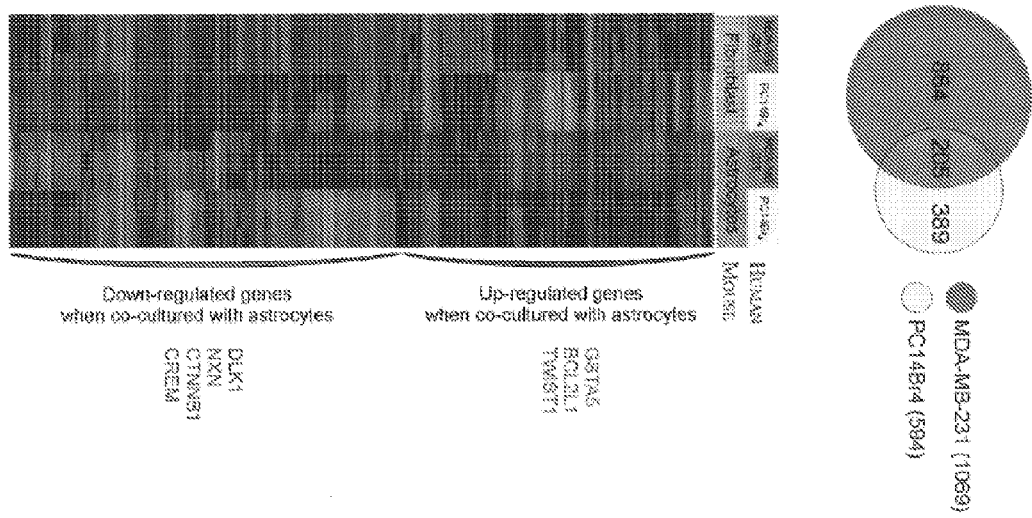
FIG. 7: In the MDA-MB-231 cells, 1069 genes, and in the PC14Br4 cells, 594 genes were differentially expressed. A two-gene list comparison revealed increased expression of several genes well known to be associated with anti-apoptosis and survival: glutathione S transferase 5 (GSTA5), BCL2L1, TWIST.
Figure 8:
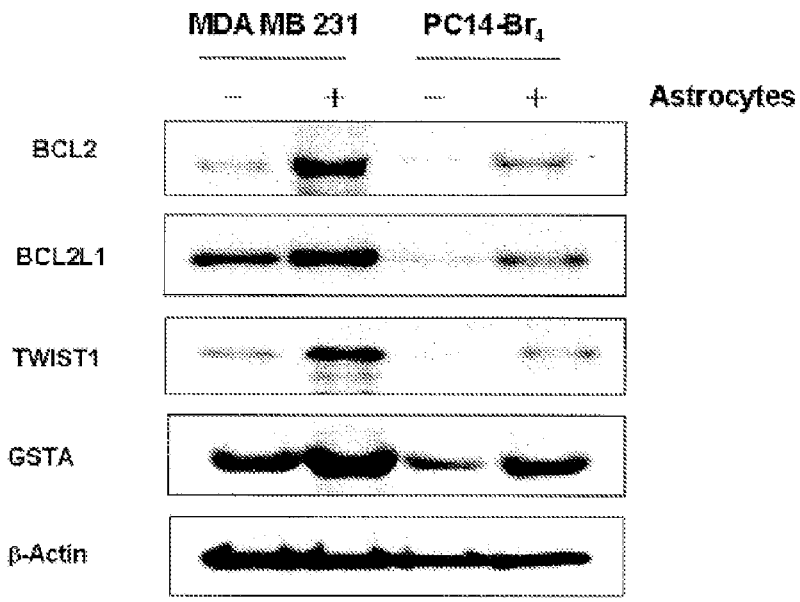
FIG. 8: The expression of several anti-apoptosis and survival genes was confirmed at the protein level by Western blot analysis.
Figure 9:
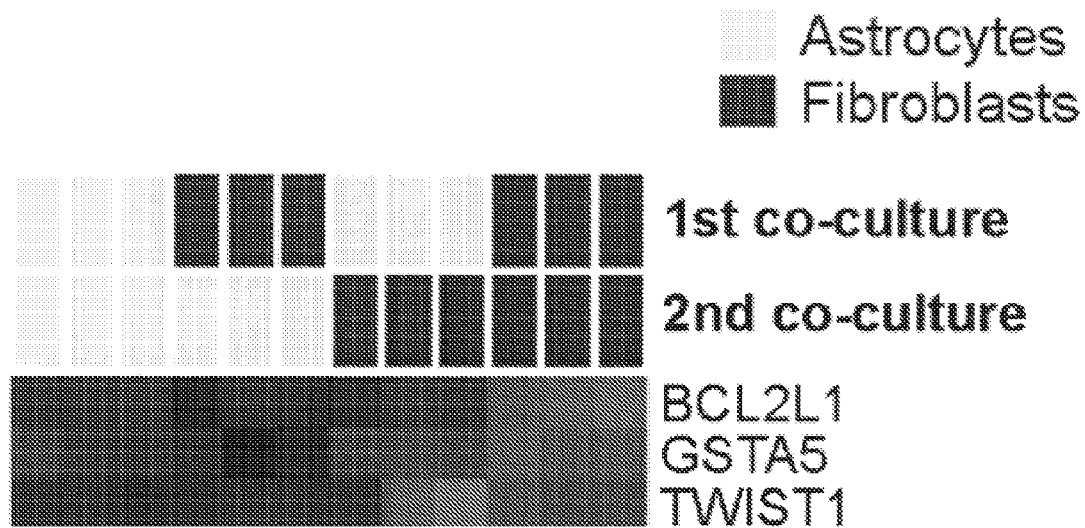
FIG. 9: Gene transcription data were collected from two cycles of co-culture experiments.

The Inventors identified tumor cell genes whose expression is commonly altered subsequent to co-culture with astrocytes by applying two-sample t tests (P<0.001). Using this procedure, the Inventors identified in the MDA-MB-231 cells, 1069 genes, and in the PC14Br4 cells, 594 genes that were differentially expressed (FIG. 7). A two-gene list comparison revealed increased expression of several genes well known to be associated with anti-apoptosis and survival: glutathione S transferase 5 (GSTA5), BCL2L1, TWIST (FIG. 7). The expression of these genes was confirmed at the protein level by Western blot analysis (FIG. 8). The Inventors then determined whether the altered gene expression pattern in tumor cells co-cultured with astrocytes (but not fibroblasts) was permanent or transient. The Inventors co-cultured tumor cells for one cycle with astrocytes or fibroblasts, and then harvested the tumor cells and plated them in a second round on astrocytes or fibroblasts. When the gene expression data were collected from the two cycles of co-culture experiments, the influence of the second co-culture was dominant in gene expression patterns of the cancer cells. Regardless of the first co-culture condition, cancer cells co-cultured with astrocytes in the second cycle exhibited a distinctive gene expression signature that was detected in the first cycle culture experiments (high expression of GSTA5, BCL2L1, and TWIST), whereas cancer cells co-cultured with astrocytes in the first round lost the specific gene expression signatures when they were co-cultured with fibroblasts in the second round (FIG. 9). This result parallels that of the in vitro chemoprotection assay results summarized in FIG. 5 and proves that the gene expression pattern in the tumor cells depends on constant contact with the astrocytes. Tumor cells co-cultured in the second round with astrocytes also expressed a high level of TCF4, CD24, CARD14, and EFNB2 genes (data not shown). Clinical studies have shown that tumor cell expression of these genes is correlated with a poor prognosis. A fourth aspect of the present invention is therefore an in vitro cell based chemoresistance assay having a molecular diagnostic component which is useful, for example, in studying the phenomenon of astrocyte mediated protection of brain metastasis cells from cytotoxic chemotherapy induced cell death in an ex vivo setting. In certain embodiments, the molecular diagnostic component is one or more of a gene expression profiling step and an analysis of cellular protein concentrations. In specific embodiments, a predetermined gene expression signature is used to evaluate the effects of experimental interventions to, e.g., abrogate astrocyte mediated protection. A fifth aspect of the invention is a gene expression signature or a combination of protein level profiles indicative of astrocyte mediated protection of brain metastasis cells from cytotoxic chemotherapy induced cell death. A sixth aspect is the process of producing said gene signature or protein level profiles as described and exemplified above.

Experiment 6

Figure 10:
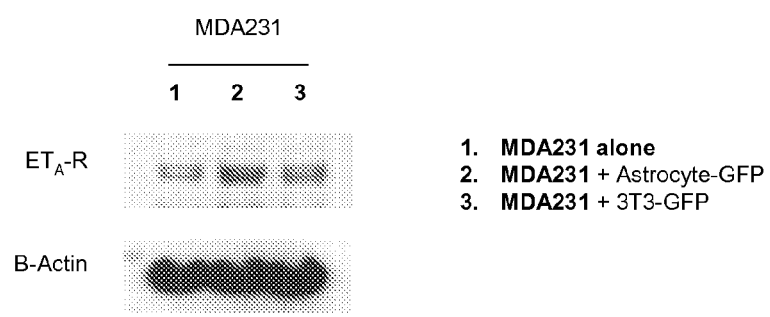
FIG. 10: Increased expression of ETA-R in MDA-MB-231 human breast cancer cells co-cultured with astrocytes but not with fibroblasts (3T3)

Expression of Endothelin Receptors by Tumor Cells and Astrocytes 300,000 MDA-MB-231 human breast cancer cells were cultured for 24 hours with 600,000 GFP-labeled astrocytes or with GFP-labeled 3T3 fibroblasts. The cells were then collected and sorted to isolate the MDA-MB-231 cells. Proteins were extracted, analyzed by Western blots, and hybridized with anti-$ET_AR$ antibody. The data shown in FIG. 10 clearly demonstrate that tumor cells co-cultured with astrocytes express a higher level of $ET_AR$.

Figure 11:
FIG. 11: Expression of pAKT by MDA-MB-231 human breast cancer cells co-cultured with astrocytes/Taxol.

In the next set of studies, 10,000 GFP-labeled MDA-MB-231 cells were co-cultured with 20,000 astrocytes in chamber slides. Twenty-four hours later, the cultures were treated for 24 hours with Taxol (15 ng/ml) and then stained for phosphorylated pAKT (4% PFA fixation). As shown in FIG. 11, tumor cells co-cultured with astrocytes (and Taxol) expressed high levels of pAKT. Hence, co-culture with astrocytes produces increased expression of ETR and survival factors by tumor cells which are correlated with tumor cell increased resistance to chemotherapeutic drugs. Similar studies with an anti-$ET_BR$ antibody revealed $ET_BR$ expression.

Experiment 7

Endothelin Receptor Antagonists do not Produce Cytotoxic Effects Against Tumor Cells Using the in vitro cell based chemoresistance assay scheme described above, the Inventors tested two endothelin receptor antagonists having dual ETAR and ETBR affinity to assess the degree of astrocyte-mediated protection against the cytotoxic effects of the chemotherapy agent. One ETR antagonist tested was Bosentan which is approved by the EMEA for use in the treatment of pulmonary artery hypertension (PAH). The second drug tested was designated ACT-064992 and is a derivative of Bosentan also having dual ETAR/ETBR affinity. ACT-064992 is formally designated Macitentan, and has the structure [N-[5-(4-bromophenyl)-6-(2-(5-bromopyrimidin-2-yloxy)ethoxy)-pyrimidin-4-yl]-N'-propylaminosulfonamide]:

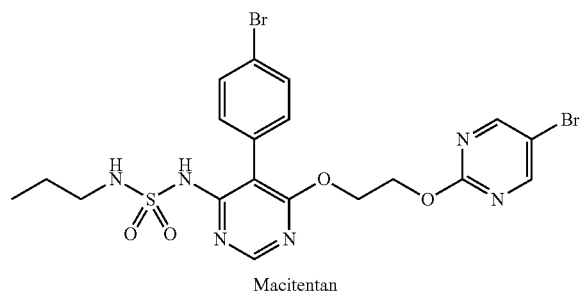 [SMILES: CCCNS(=O)(=O)Nc1ncnc(OCCOc2ncc(Br)cn2)c1-c1ccc(Br)cc1]

Macitentan

Iglarz M, et al., Pharmacology of macitentan, an orally active tissue-targeting dual endothelin receptor antagonist, J Pharmacol Exp Ther. 2008 December; 327(3):736-45. Epub 2008 Sep. 9. The original disclose of the ACT-064992 molecule, its synthesis and its pharmacological activity may be found in WO02/053557. ACT-064992 is roughly three times more pharmaceutically active than Bosentan (i.e. it requires ⅓ the dose). The detailed data herein refer to the ACT-064992 experiments, however analogous results are achieved by higher dose Bosentan experiments.

Figure 12:
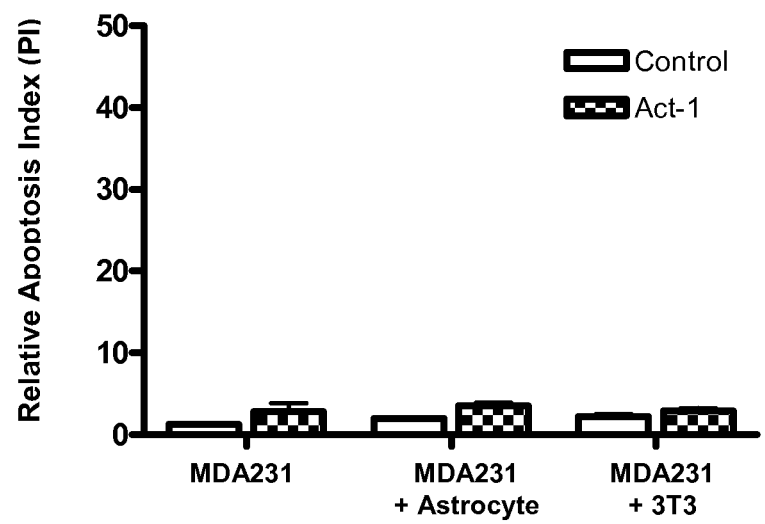
FIG. 12: ACT-064992 added alone to MDA-MB-231 human breast cancer cells or with astrocytes or with 3T3 fibroblasts did not produce any measurable cytotoxic effects.
Figure 13:
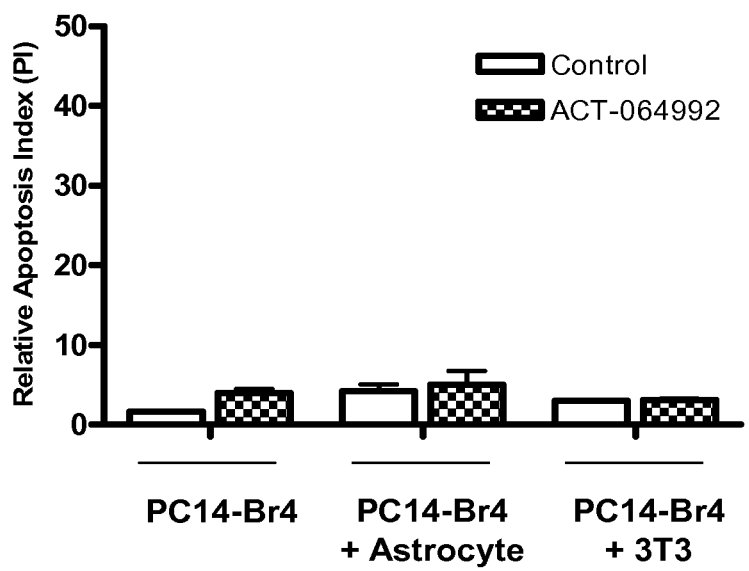
FIG. 13: ACT-064992 added alone to PC14 lung cancer cells or with astrocytes or with 3T3 fibroblasts did not produce any measurable cytotoxic effects.
Figure 14A:
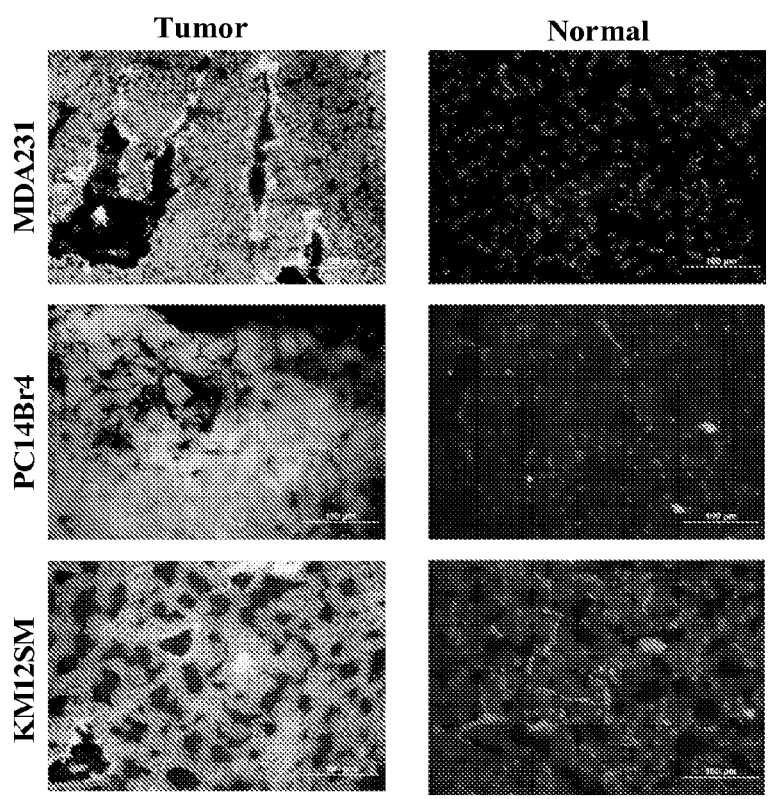
FIG. 14A-D: Immunostaining for $ET_AR$ and $ET_BR$ in several in vivo experimental models for metastatic brain cancer shows relatively high expression associated specifically with tumors and not normal brain tissues.
Figure 14B:
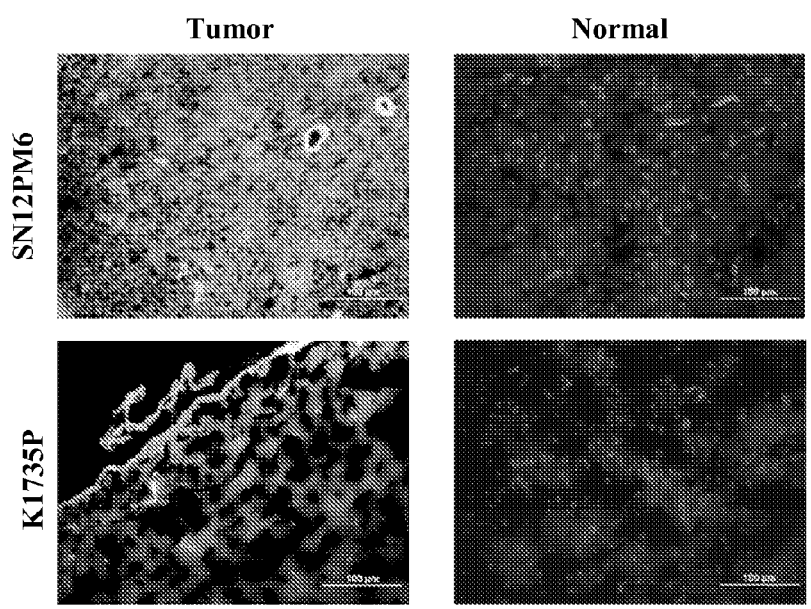
Figure 14C:
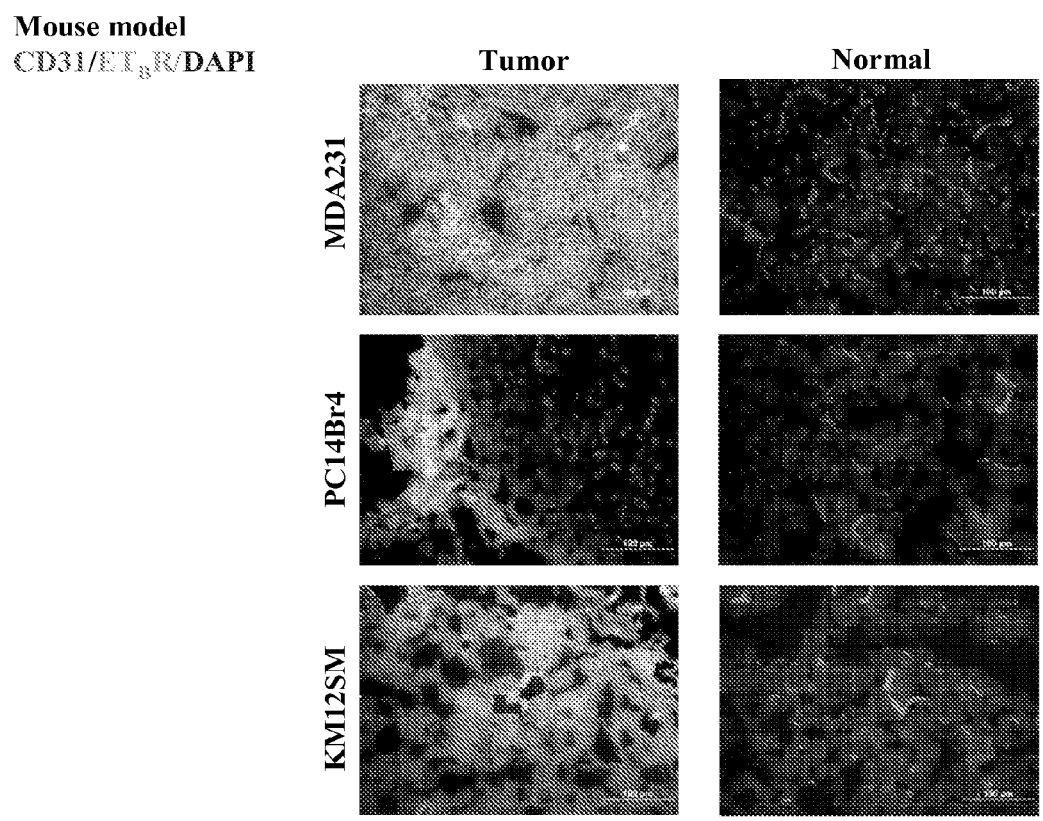
Figure 14D:
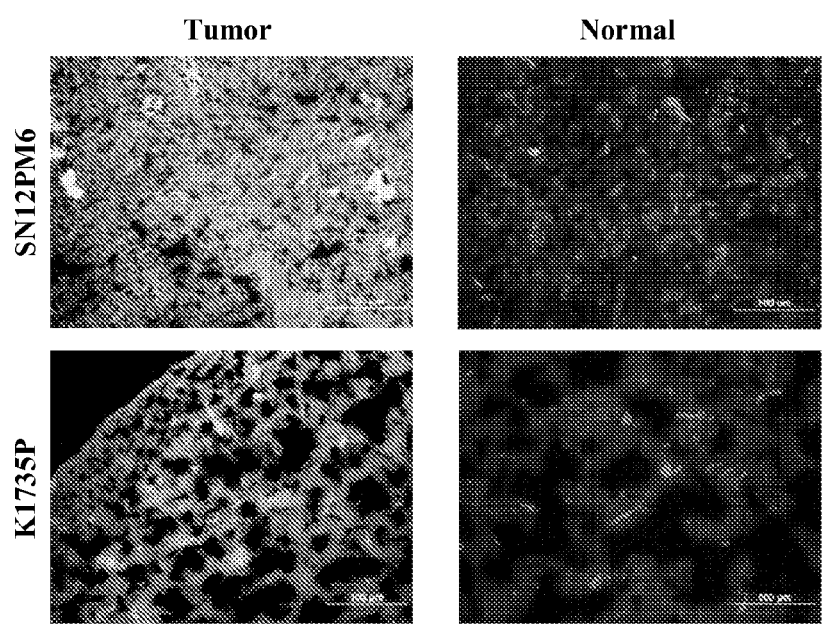

ACT-064992 (100 nM) was added to the cell-based co-culture assay described above with a tumor cell:astrocyte cell ratio of 1:2 or tumor cell:3 T3 fibroblasts for 48 hours, and the degree of apoptosis was measured as described above. As shown in FIG. 12 (MDA-231 breast cancer) and FIG. 13 (PC14 lung cancer), ACT-064992 added alone or with astrocytes or with 3T3 fibroblasts did not produce any measurable cytotoxic effects.

Experiment 8

Endothelin Receptor Antagonists in Combination with Chemotherapeutic Agents

Figure 15:
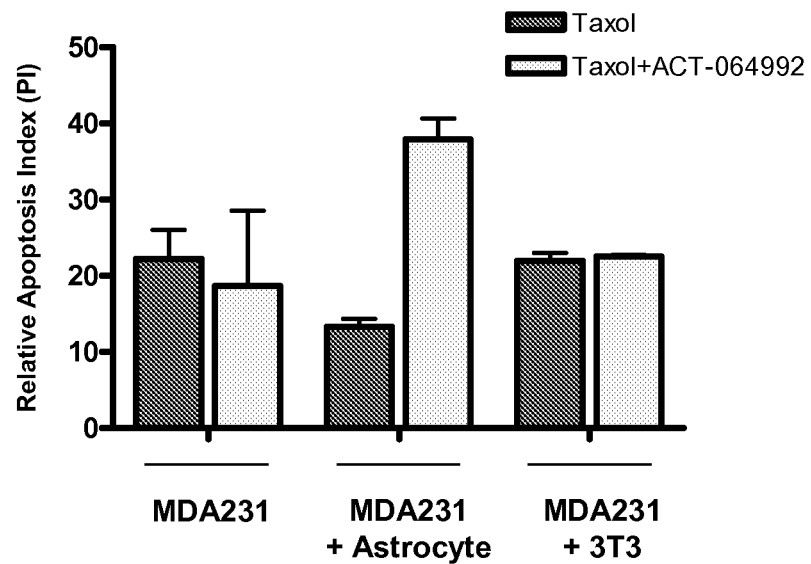
FIG. 15: Combination therapy of paclitaxel and ACT-064992 on MDA-MB-231 human breast cancer cells co-cultured with astrocytes or with 3T3 fibroblasts.
Figure 16:
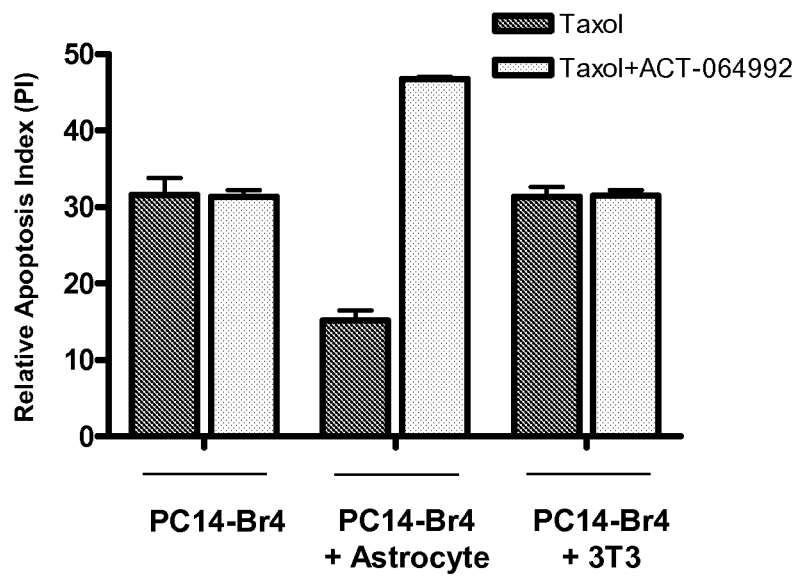
FIG. 16: Combination therapy of paclitaxel and ACT-064992 on human lung cancer cells PC14Br4 co-cultured with astrocytes or with 3T3 fibroblasts.
Figure 17:
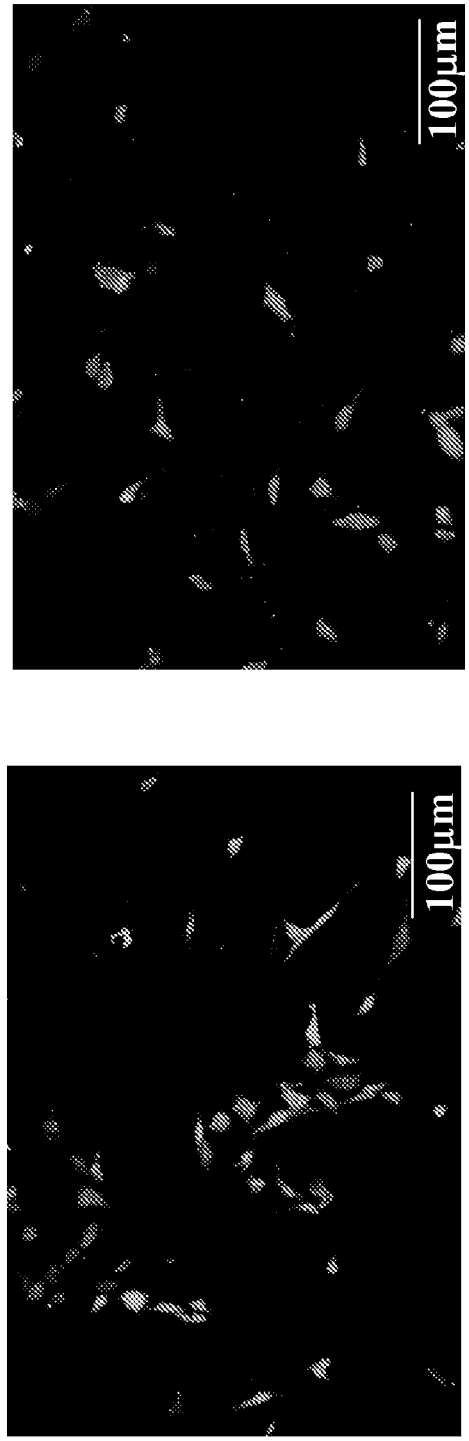
FIG. 17: The addition of ACT-064992 to co-cultures of astrocytes and tumor cells inhibited the expression of the survival factors pAKT and pMAPK.

ETR antagonists as shown above were ineffective as a single agent chemotherapy. This negative result made the dramatic effect seen with ETR antagonists as a component of combination therapies highly unexpected. In co-culture experiments, cell culture ratios were 1:2 tumor cell:astrocyte cell (50, 000:100,000), and treatments were using paclitaxel (TAXOL®) (6 ng/ml) and/or ACT-064992 (100 nM) for 48 hours (FIG. 15; *p<0.01). For the control experiments using MDA-MB-231 cells, the same astrocyte-mediated protection from paclitaxel occurred as in prior experiments. There were two surprising results from these combination experiments. First, the combination of paclitaxel and ACT-064992 in the controls lacking astrocytes did not yield a significant increase in cell death over paclitaxel alone. This was seen in at least three independent experiments (FIG. 15). These results were reproduced using human lung cancer cells PC14Br4 (FIG. 16). Thus, under the conditions tested, ETR antagonists were also ineffective in combination as was observed in Experiment 6 as a single agent. In the tumor cell-astrocyte co-cultures, ACT-064992 showed the unexpected ability to negate the astrocyte-mediated protection from paclitaxel. Even more surprising, ACT-064992 actually enhanced the efficacy of paclitaxel, as compared to control experiments without astrocytes, to super-sensitize the metastatic tumor cells to paclitaxel. The addition of ACT-064992 to co-cultures of astrocytes and tumor cells inhibited the expression of the survival factors pAKT and pMAPK (FIG. 17).

This inhibition was directly correlated with the increased tumor cell death mediated by the chemotherapeutic drug. This synergism is made even more surprising because the experiments lacking astrocytes did not demonstrate even additive effects. These dramatic results demonstrate the importance of the new co-culture screening methods disclosed herein because the effects of ETR antagonists in combination therapy would not have been seen in a standard tumor cell line assay scheme lacking co-cultured astrocytes. A seventh aspect of the present invention is thus the use of endothelin receptor antagonists in combination with one or more other cytotoxic chemotherapy agents and/or radiation therapy to treat an existing brain metastasis tumor in a subject. In particular embodiments, this combination therapy super-sensitizes the existing brain metastasis to the cytotoxic chemotherapy agents and/or radiation therapy co-administered with the ETR antagonist.

In Vivo Endothelin Receptor Antagonist Therapy for Existing Brain Metastasis

In vivo delivery of endothelin receptor antagonist(s) and co-administered chemotherapy agents may be achieved by the same oral and or systemic delivery already developed and used in prior clinical trials for various members of this class of compounds. The development and optimization of such therapeutic regimens is routine in the art. [Clinical trials: a practical guide to design, analysis and reporting Edited by Ameet Bakhai and Duolao Wang. Remedica, London 2005.] One issue specific to brain cancers is the impact of the blood brain barrier. While this has been long cited as a technical problem precluding systemic treatments for brain metastasis, the art has now recognized that even in micrometastasis, the blood brain barrier is partially disrupted. [Cavaliere R. and Schiff D., Chemotherapy and cerebral metastases: misperception or reality? Neurosurg Focus. 2007 Mar. 15; 22(3): E6.] Thus it is reasonable to expect that systemic delivery of endothelin receptor antagonist(s) will penetrate and have therapeutic effect in brain metastasis tumors. In addition, certain members of the endothelin receptor antagonist(s) family have the ability to cross even intact blood brain barrier, thus rendering them particularly suited for use in brain metastasis tumor therapy in vivo. [Vatter H, et al., Cerebrovascular characterization of clazosentan, the first nonpeptide endothelin receptor antagonist shown to be clinically effective for the treatment of cerebral vasospasm. Part II: effect on endothelin(B) receptor-mediated relaxation. J Neurosurg. 2005 June; 102(6):1108-14.] Finally, direct tumor infusion or injection of endothelin receptor antagonist(s) may be suitable where the size of metastatic tumors render such an approach feasible.

In Vivo Therapy for Brain Metastasis in Mice

To further validate the efficacy of endothelin receptor antagonist therapy for existing brain metastasis, the Inventors performed exemplary in vivo experiments using mice. Nude mice were injected with 10,000 viable MDA231 cells mice by way of the internal carotid artery. Preliminary pathology work revealed that visible established metastases formed two weeks, post injection (data not shown). The Inventors thus started treatments at this time point.

Experiment 9

ACT-064992 and Temozolomide Effects on In Vivo Tumor Growth

Figure 18E:
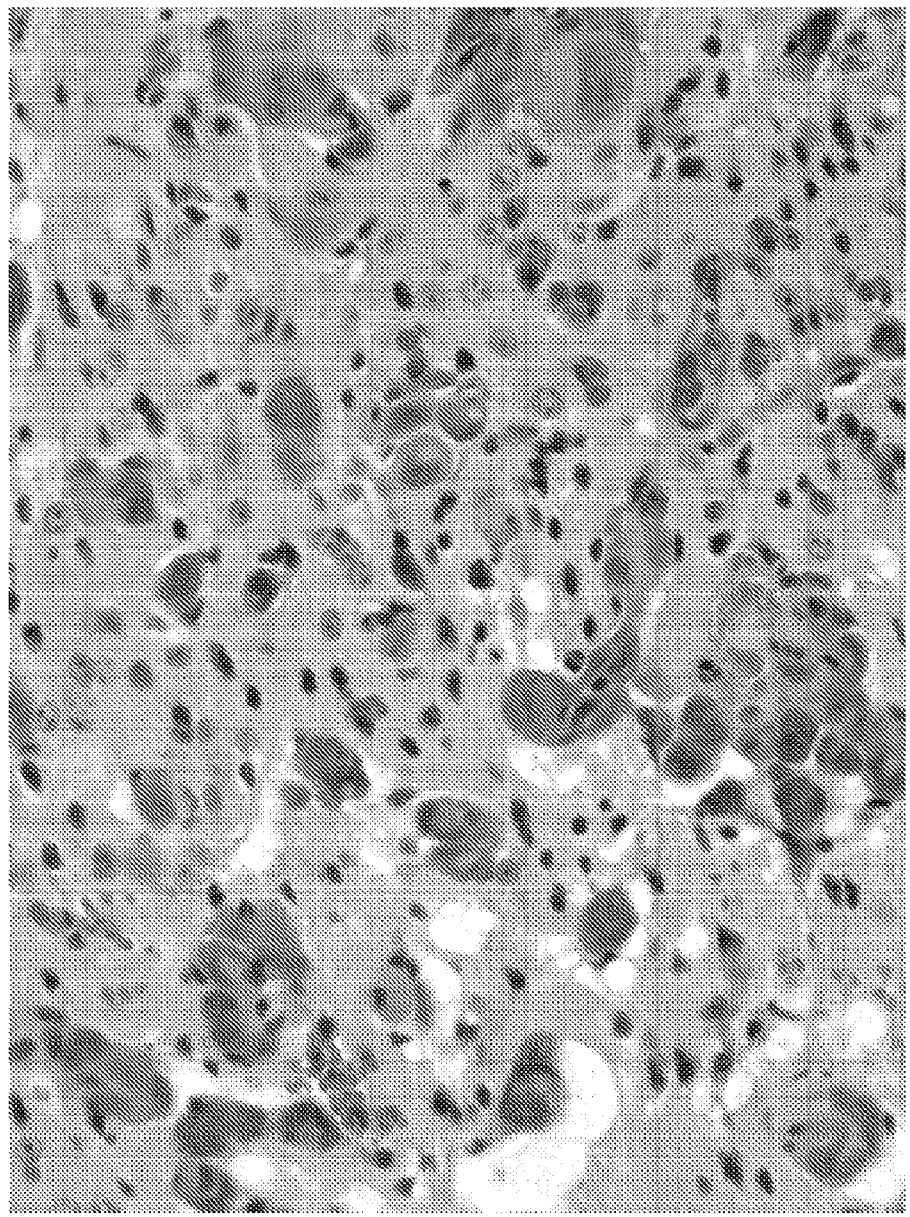
FIG. 18: Brain sections were fixed and stained for brain metastasis visualization. Control (vehicle) (FIG. 18A); temozolomide ("TMA") 10 mg/kg p.o., daily (FIG. 18B); ACT-064992 50 mg/kg, p.o. daily (FIG. 18C); or combination TMZ+ACT-064992 (FIG. 18D); combination TMZ+ACT-064992 at higher magnification (FIG. 18E)

Nude mice were injected into the internal carotid artery with 10,000 viable MDA231 cells. The treatment groups at two weeks post injection were: Control (vehicle) (FIG. 18A); temozolomide ("TMZ") 10 mg/kg p.o., daily (FIG. 18B); ACT-064992 50 mg/kg, p.o. daily (FIG. 18C); or combination TMZ+ACT-064992 (FIG. 18D).

All mice were killed on day 28 of treatment. Brain sections were fixed and stained. Brain metastases were evaluated visually. Exemplary specimens are shown in FIG. 18A-D at the same magnifications. As can be seen in more detail in FIG. 18E, the combination TMZ and ACT-064992 dramatically reduced the size and density of metastasis tumors compared to TMZ alone. This demonstrates that the above described cell culture system results correlate directly with the observed effects in vivo.

Experiment 10

ACT-064992 and Paclitaxel Effects on In Vivo Tumor Growth

Figure 19:
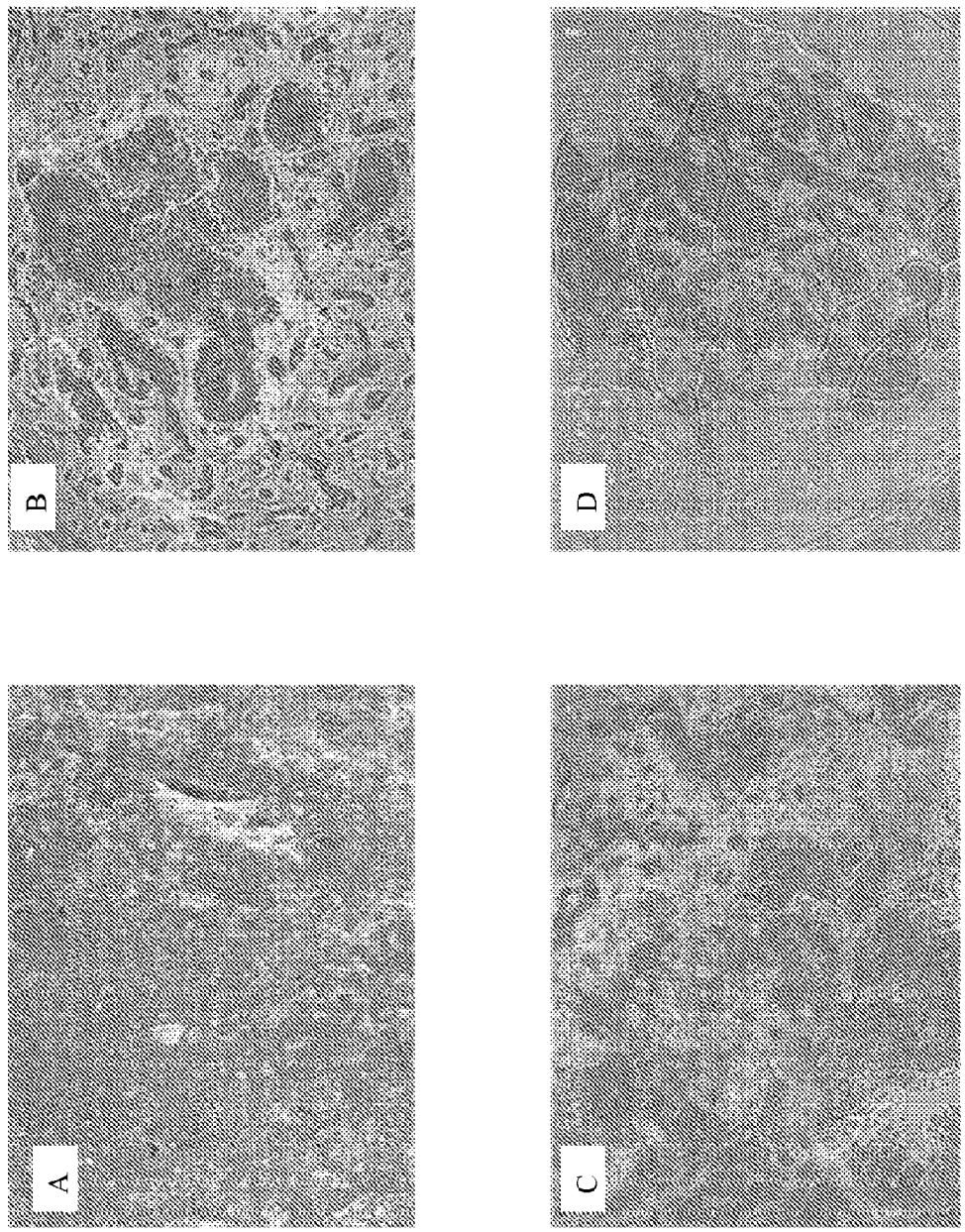
FIG. 19: Brain sections were fixed and stained for brain metastasis visualization. A. Control (injected with vehicle solution); B. Paclitaxel (8 mg/kg administered intraperitoneally once per week); C. ACT-064992 (50 mg/kg administered orally once per day); and D. Combination of ACT-064992 and paclitaxel.

Female nude mice (10-12 weeks old) were injected in the internal carotid artery with 10,000 viable MDA231 cells. Two weeks after the injection when brain metastases were established, the mice were randomized into 4 treatment groups (n=10): 1) Control (injected with vehicle solution); 2) Paclitaxel (8 mg/kg administered intraperitoneally once per week); 3) ACT-064992 (50 mg/kg administered orally once per day); and 4) Combination of ACT-064992 and Paclitaxel. All mice were euthanized after 28 days of treatment and autopsied. The brains were collected for histologic study and immunohistochemistry. Exemplary results are shown in FIG. 19. A. Control (19A), ACT-064992 (19B) and Paclitaxel (19C) all have well defined metastatic tumors. The ACT-064992+Paclitaxel group (19D) in contrast had much smaller colonies of tumor cells.

The results with temozolomide and paclitaxel demonstrate that endothelin receptor antagonist therapy sensitizes brain metastasis to chemotherapy agents generally.

Experiment 11

ACT-064992 and Paclitaxel Effects on In Vivo Tumor Cell Proliferation

Figure 20:
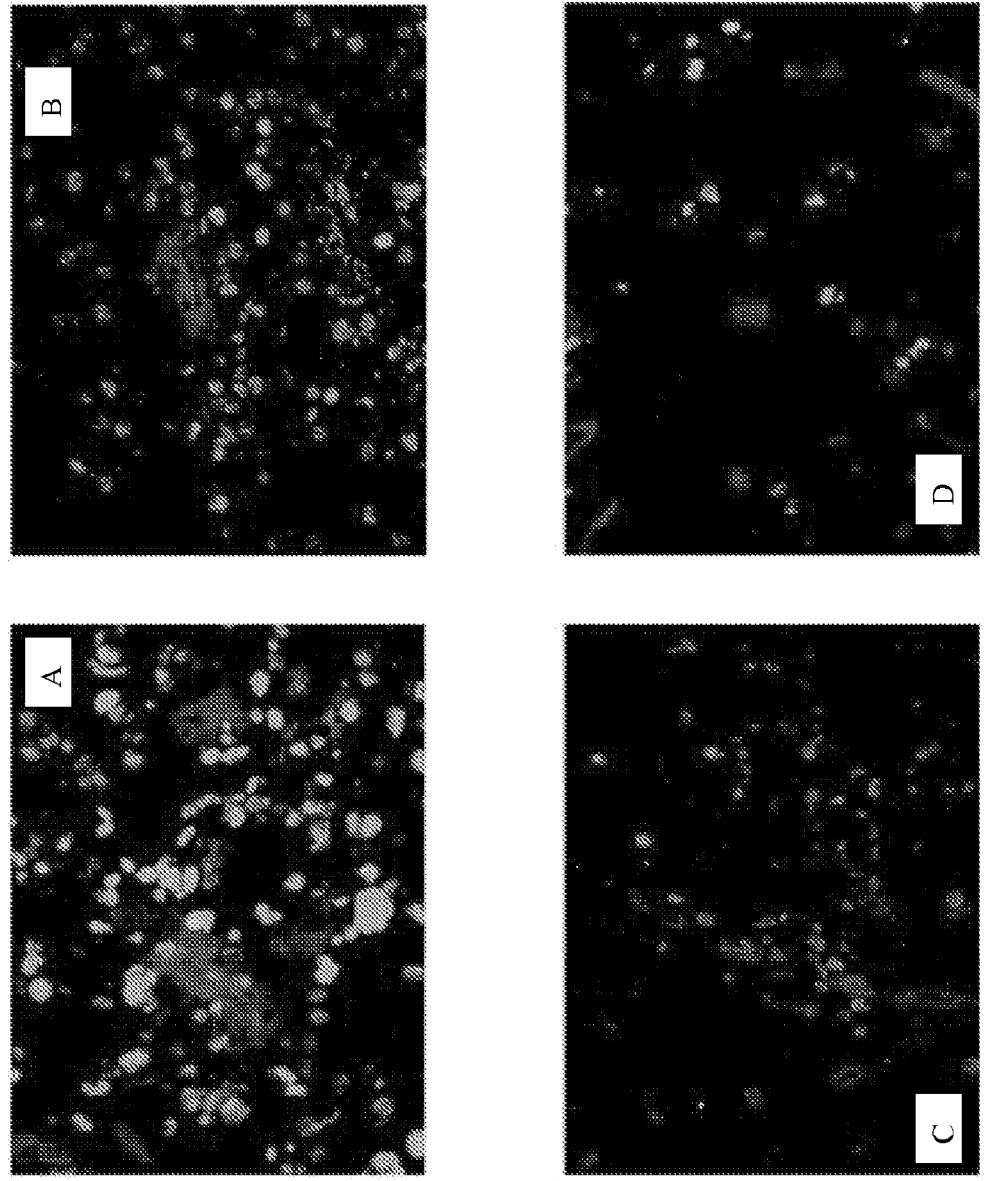
FIG. 20: Representative brain slices from the four treatment groups were stained for CD31 (endothelial cell marker) and Ki67 (cell proliferation marker): A. control mice; B. mice treated with only paclitaxel; C. ACT-064992; D. paclitaxel and ACT-064992.

Representative brain slices from the four treatment groups were stained for CD31 (endothelial cell marker) and Ki67 (cell proliferation marker). The brains of control mice, mice treated with only paclitaxel, or only ACT-064992 contained a large number of proliferating cells. In sharp contrast, the brains of mice treated with both paclitaxel and ACT-064992 contained only a few dividing cells. FIGS. 20A, B, C and D, respectively.

Experiment 12

ACT-064992 and Paclitaxel Effects on In Vivo Tumor Cell Apoptosis

Figure 21:
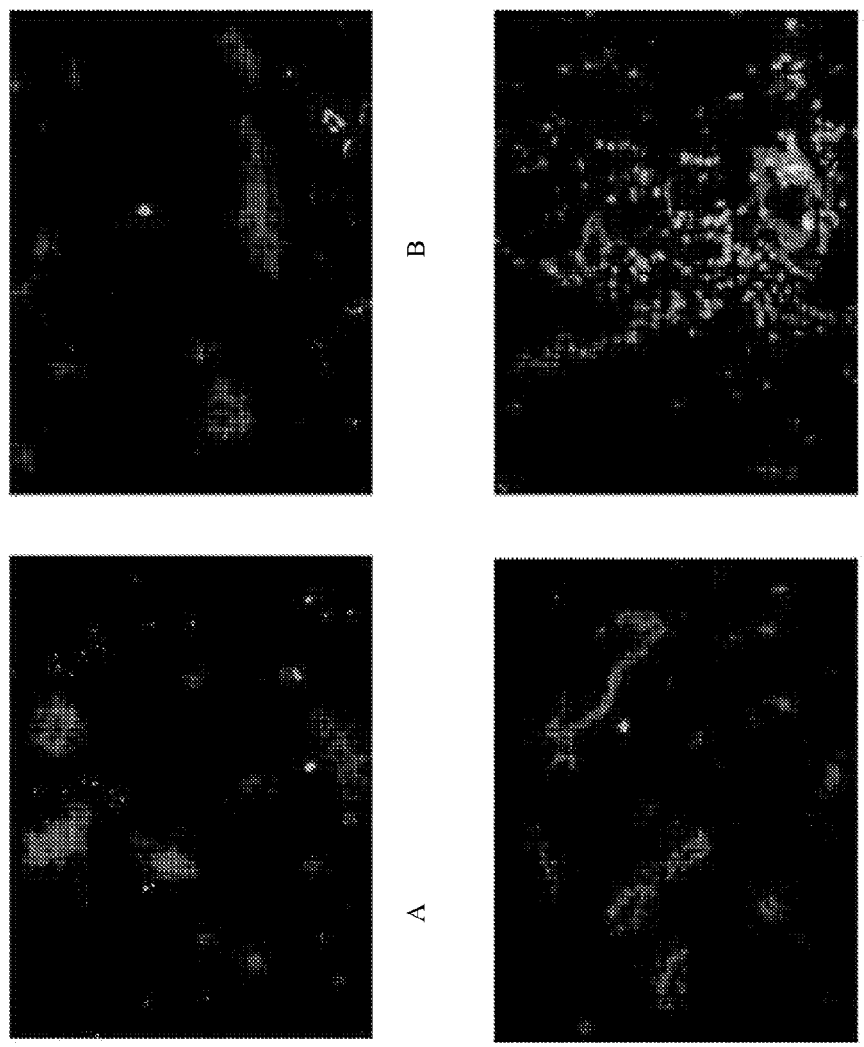
FIG. 21: Brain slices of mice from different treatment groups were analyzed by in situ Terminal deoxynucleotidyl transferase dUTP nick end labeling (TUNEL): A. control; B. paclitaxel-treated; C. ACT-064992-treated; D. Combination of ACT-064992 plus paclitaxel.

Brain slices of mice from different treatment groups were analyzed by in situ Terminal deoxynucleotidyl transferase dUTP nick end labeling (TUNEL). Negoescu A, et al., J Histochem Cytochem. 1996 September; 44(9):959-68. The brains of control, Taxol-treated, and ACT-064992-treated mice had few to no apoptotic cells. FIG. 21A-C. In sharp contrast, the brains of mice treated with the combination of ACT-064992 plus Taxol had a large number of apoptotic tumor cells (green) and endothelial cells (yellow) (FIG. 21D).

Experiment 13

Figure 22:
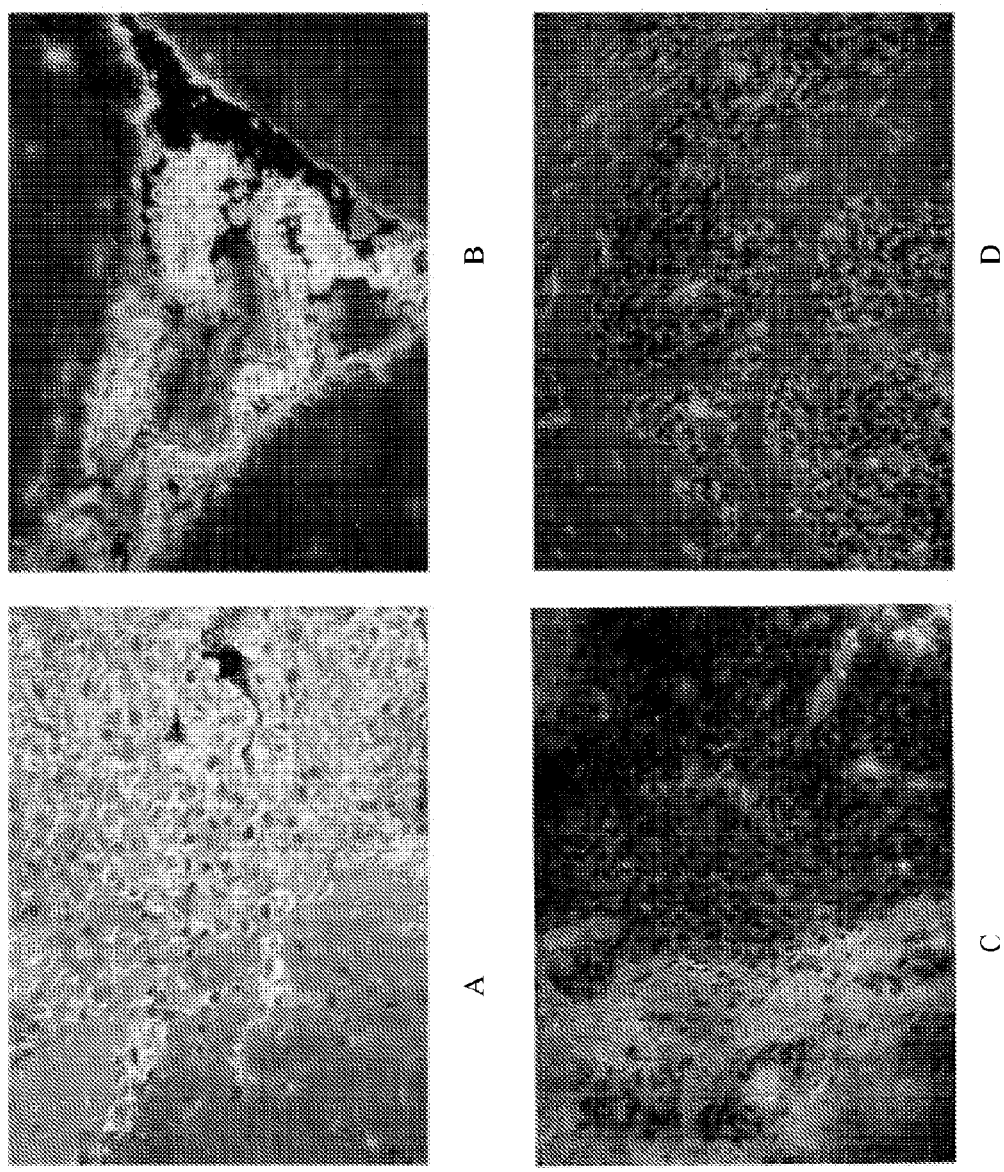
FIG. 22: Brain slices of mice from the four treatment groups were immunostained for $ET_A$ (red) and phosphoserine (green) colocalization produced orange-yellow color. A. Control brain; B. brain from mice treated with paclitaxel; C. brain from mice treated with ACT-064992 alone; D. brain from mice treated with ACT-064992+paclitaxel.
Figure 23:
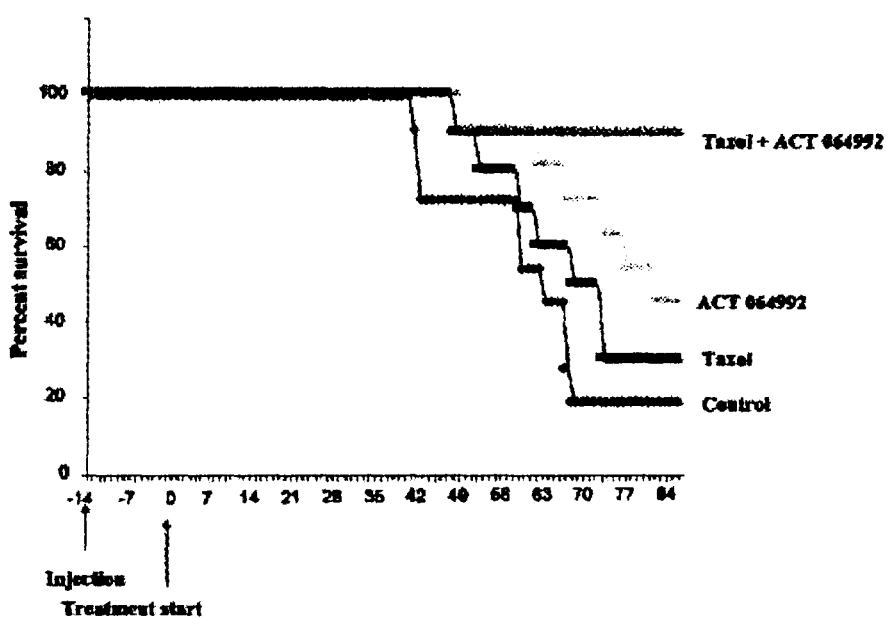
FIG. 23: Results of Survival Study for Treatment of Experimental Human MDA231 Breast Cancer Brain Metastasis with ACT064992 and Taxol.

Brain slices of mice from the four treatment groups were immunostained for $ET_AR$ (red) and phosphoserine (green) colocalization produced orange-yellow color. Control brains expressed phosphorylated $ET_AR$ as did brains from mice treated with paclitaxel (FIG. 22A-B). Treatment with ACT-064992 alone, and with ACT-064992+paclitaxel, prevented phosphorylation of the $ET_AR$. (FIG. 22C-D). This result confirms the correlation of endothelin receptor antagonist activity and the sensitization metastatic tumors to chemotherapy agents.

Experiment 14

Survival Study for Treatment of Experimental Human MDA231 Breast Cancer Brain Metastasis with ACT064992 and Taxol Experimental Details $5 \times 10^3$ MDA231 cells were injected according to the protocol in Experiment 10. Treatment began on day 14 after injection according to the protocol in Experiment 10. A Survival curve is drawn and the p-value derived to compare the statistical significance among treatment groups.

Treatment Groups

Control (vehicle): daily oral administrations and once weekly i.p. injections.

Paclitaxel (5 mg/kg): daily oral vehicle administrations and once weekly i.p. injection of Paclitaxel.

ACT064992 (10 mg/kg): daily oral ACT064992 administrations and once weekly i.p. injections of Paclitaxel.

Results

Day of death (after treatment)

Control: 42, 43, 53, 60, 64, 68, 68, 69, 69

Paclitaxel: 49, 53, 60, 63, 74, 74, 78

ACT064992: 51, 63, 68, 75, 78, 82

Paclitaxel+ACT: 48

Test for the Determination of $ET_A$ or $ET_B$ $IC_{50}$:

For competition binding studies, membranes of CHO cells expressing human recombinant $ET_A$ or $ET_B$ receptors are used. Microsomal membranes from recombinant CHO cells are prepared and the binding assay made as previously described (Breu V., et al, *FEBS Lett.* (1993), 334, 210).

The assay is performed in 200 μL 50 mM Tris/HCl buffer, pH 7.4, including 25 mM $MnCl_2$, 1 mM EDTA and 0.5% (w/v) BSA in polypropylene microtiter plates. Membranes containing 0.5 ug protein were incubated for 2 h at 20° C. with 8 pM [$^{125}$I]ET-1 (4000 cpm) and increasing concentrations of unlabelled antagonists. Maximum and minimum binding are estimated in samples without and with 100 nM ET-1, respectively. After 2 h, the membranes are filtered on filterplates containing GF/C filters (Unifilterplates from Can berra Packard S.A. Zurich, Switzerland). To each well, 50 μL of scintillation cocktail is added (MicroScint 20, Can berra Packard S.A. Zürich, Switzerland) and the filter plates counted in a microplate counter (TopCount, Can berra Packard S.A. Zürich, Switzerland).

All the test compounds are dissolved, diluted and added in DMSO. The assay is run in the presence of 2.5% DMSO which is found not to interfere significantly with the binding. $IC_{50}$ is calculated as the concentration of antagonist inhibiting 50% of the specific binding of ET-1.

BACKGROUND REFERENCES

1. HAM Mucke "Small-molecule endothelin receptor antagonists: A review of patenting activity across therapeutic areas" *IDrugs* 2009 12:366-375.
2. Yoshimine T, et al. (1985) Immunohistochemical study of metastatic brain tumors with astroprotein (GFAP), a glia-specific protein. Tissue architecture and the origin of blood vessels. *J Neurosurg* 62: 414-418.
3. Nelson J B, et al., Phase 3, randomized, controlled trial of atrasentan in patients with nonmetastatic, hormone-refractory prostate cancer. *Cancer.* 2008 Nov. 1; 113(9):2376-8.
4. Chiappori A A, et al. Phase I/II study of atrasentan, an endothelin A receptor antagonist, in combination with paclitaxel and carboplatin as first-line therapy in advanced non-small cell lung cancer. *Clin Cancer Res.* 2008 Mar. 1; 14(5):1464-9.
5. Carden C P, et al., Eligibility of patients with brain metastases for phase I trials: time for a rethink? *The Lancet Oncology*, Volume 9, Issue 10, Pages 1012-1017, October 2008 doi:10.1016/S1470-2045(08)70257-2.
6. Johanna A. Joycel & Jeffrey W. Pollard, Microenvironmental regulation of metastasis, *Nature Reviews Cancer* 9, 239-252 (April 2009)|doi:10.1038/nrc2618
7. Cavaliere R. and Schiff D., Chemotherapy and cerebral metastases: misperception or reality? *Neurosurg Focus.* 2007 Mar. 15; 22(3):E6.
8. Vatter H, et al., Cerebrovascular characterization of clazosentan, the first nonpeptide endothelin receptor antagonist shown to be clinically effective for the treatment of cerebral vasospasm. Part II: effect on endothelin(B) receptor-mediated relaxation. *J Neurosurg.* 2005 June; 102(6): 1108-14.
9. Iglarz M, et al., Pharmacology of macitentan, an orally active tissue-targeting dual endothelin receptor antagonist, J Pharmacol Exp Ther. 2008 December; 327(3):736-45. Epub 2008 Sep. 9.
10. WO 02/053557

TECHNICAL REFERENCES

S. Yano et al. Clin. Cancer Res. 6, 957-965 (2000).
S. J. Kim et al. J Natl. Cancer Inst. 98, 783-793 (2006).
D. Chelouche Lev et al. Clin. Cancer Res. 11, 306-314 (2005).
R. R. Langley et al. Cancer Res. 64, 3727-3730 (2004).
T. Dull et al. I Virol. 72, 8463-8471 (1998)
J. Galipeau et al. Cancer Res. 59, 2384-2394 (1999).
L. Zamai et al. Cytometry 44, 57-64 (2001).
D. Fan et al. Cancer Res. 50, 3619-3626 (1990).
M. H. Wade, J. E. Trosko, M. Schindler, Science 232, 525-528 (1986).
J. H. Lin et al. Nat. Neurosci. 1, 494-500 (1998).
P. C. Fonseca et al. Cytometry 69A, 487-493 (2006).
B. M. Bolstad, R. A. Irizarry, M. Astrand, T. P. Speed, Bioinformatics 19, 185-193 (2003).
Cory A H, Owen T C, Barltrop J A, Cory J G (July 1991). "Use of an aqueous soluble tetrazolium/formazan assay for cell growth assays in culture." *Cancer communications* 3 (7): 207-12.
Clinical trials: a practical guide to design, analysis and reporting Edited by Ameet Bakhai and Duolao Wang. Remedica, London 2005.
Negoescu A, et al., J Histochem Cytochem. 1996 September; 44(9):959-68.

All References cited or otherwise identified herein are hereby incorporated by reference in their entireties and particularly for any specific information for which they are cited.

We claim:

1. A method of inhibiting an astrocyte mediated protection of a brain metastasis cell from a cytotoxic chemotherapy induced cell death, comprising administering an effective amount of an endothelin receptor antagonist to the brain metastasis cell and the astrocyte thereby inhibiting the astrocyte mediated protection, wherein the endothelin receptor antagonist is macitentan.

2. The method of claim 1, further comprising administering at least one cytotoxic chemotherapeutic agent to the brain metastasis cell.

3. The method of claim 2, wherein the cytotoxic chemotherapy agent comprises paclitaxel, adriamycin, vinblastine, vincristine, 5-fluoro-1H-pyrimidine-2,4-dione, cisplatinum, cyclophosphamide, etoposide, teniposide, mitomycin, irinotecan, vinorelbine, etoposide, ifosfamide, temozolomide, or combinations thereof.

4. The method of claim 2, wherein the brain metastasis cell is located in an existing brain metastasis tumor in a subject or is an isolated cell.

5. The method of claim 4, wherein the brain metastasis cell is located in an existing brain metastasis tumor in a subject and said existing brain metastasis tumor is a micrometastasis.

6. The method of claim 5, wherein the existing brain metastasis tumor is a lung cancer, breast cancer, colon cancer, melanoma, or renal carcinoma brain metastasis tumor.

7. The method of claim 5, wherein the subject is a human.

8. The method of claim 7, further comprising a standard of care, wherein the standard of care is palliative care, whole brain radiotherapy, stereotactic radiosurgery or combinations thereof.

9. The method of claim 4, wherein the brain metastasis cell is located in an existing brain metastasis tumor in a subject and the existing brain metastasis tumor is a visible tumor.

10. A method of treating an existing brain metastasis tumor in a subject comprising administering an endothelin receptor antagonist and at least one cytotoxic chemotherapeutic agent, wherein the endothelin receptor antagonist is macitentan.

11. A method for administering a cytotoxic chemotherapy to treat a brain metastasis in a patient comprising
  a. administering an effective amount of endothelin receptor antagonist to desensitize astrocyte mediated protection of a brain metastasis cell from a cytotoxic chemotherapy induced cell death, wherein the endothelin receptor antagonist is macitentan; and
  b. further administering a cytotoxic chemotherapy agent to induce cell death.

12. A method of inhibiting in a human an astrocyte mediated protection of a brain metastasis cell from a cytotoxic chemotherapy induced cell death, wherein the brain metastasis cell is located in an existing brain metastasis tumor in said human or is an isolated cell, and said existing brain metastasis tumor is a micrometastasis, said method comprising:
  a. administering an effective amount of an endothelin receptor antagonist to the brain metastasis cell and the astrocyte thereby inhibiting the astrocyte mediated protection, wherein the endothelin receptor antagonist is macitentan;

b. administering at least one cytotoxic chemotherapeutic agent to the brain metastasis cell; and
c. further performing whole brain radiotherapy, stereotactic radiosurgery, or combinations thereof.

13. A method of inhibiting in a human an astrocyte mediated protection of a brain metastasis cell from a cytotoxic chemotherapy induced cell death, wherein the brain metastasis cell is located in an existing brain metastasis tumor in said human or is an isolated cell, and said existing brain metastasis tumor is a visible tumor, said method comprising:
a. administering an effective amount of an endothelin receptor antagonist to the brain metastasis cell and the astrocyte thereby inhibiting the astrocyte mediated protection, wherein the endothelin receptor antagonist is macitentan;
b. administering at least one cytotoxic chemotherapeutic agent to the brain metastasis cell; and
c. further performing whole brain radiotherapy, stereotactic radiosurgery, or combinations thereof.

* * * * *